(12) United States Patent
Choi et al.

(10) Patent No.: US 10,327,738 B2
(45) Date of Patent: Jun. 25, 2019

(54) ULTRASOUND IMAGING APPARATUS AND METHOD OF PROCESSING ULTRASOUND IMAGE THEREOF

(71) Applicant: SAMSUNG ELECTRONICS CO., LTD., Suwon-si (KR)

(72) Inventors: Ki-wan Choi, Anyang-si (KR); Hyoung-ki Lee, Seongnam-si (KR); Jun-ho Park, Hwaseong-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 58 days.

(21) Appl. No.: 15/002,018

(22) Filed: Jan. 20, 2016

(65) Prior Publication Data

US 2016/0287215 A1  Oct. 6, 2016

(30) Foreign Application Priority Data

Mar. 31, 2015 (KR) .................. 10-2015-0045331
Aug. 17, 2015 (KR) .................. 10-2015-0115415

(51) Int. Cl.
*A61B 8/08* (2006.01)
*A61B 8/00* (2006.01)

(52) U.S. Cl.
CPC .............. *A61B 8/485* (2013.01); *A61B 8/463* (2013.01); *A61B 8/469* (2013.01); *A61B 8/5207* (2013.01); *A61B 8/5223* (2013.01); *A61B 8/56* (2013.01); *A61B 8/4472* (2013.01); *A61B 8/464* (2013.01); *A61B 8/483* (2013.01); *A61B 8/488* (2013.01)

(58) Field of Classification Search
None
See application file for complete search history.

(56) References Cited

U.S. PATENT DOCUMENTS

| | | | |
|---|---|---|---|
| 7,252,004 B2 | 8/2007 | Fink et al. | |
| 7,444,875 B1 * | 11/2008 | Wu .................... | A61B 8/08 600/438 |
| 8,187,187 B2 * | 5/2012 | Fan .................... | A61B 8/00 600/438 |
| 8,298,143 B2 | 10/2012 | Kanai et al. | |
| 8,961,418 B2 * | 2/2015 | Fan .................... | A61B 8/485 600/438 |
| 9,895,137 B2 | 2/2018 | Tabaru et al. | |

(Continued)

FOREIGN PATENT DOCUMENTS

| | | |
|---|---|---|
| CN | 103619260 A | 3/2014 |
| CN | 104203112 A | 12/2014 |

(Continued)

OTHER PUBLICATIONS

Communication dated Aug. 29, 2016 issued by European Patent Office in counterpart European Patent Application No. 16162860.7.

(Continued)

*Primary Examiner* — James M Kish
(74) *Attorney, Agent, or Firm* — Sughrue Mion, PLLC

(57) ABSTRACT

An ultrasound imaging apparatus and a method for operating the ultrasound imaging apparatus are provided. When providing an elasticity value to a user, the reliability of the elasticity value is provided to the user to enable the user to easily determine whether the elasticity value is an appropriate value.

20 Claims, 17 Drawing Sheets

(56) References Cited

U.S. PATENT DOCUMENTS

| | | | |
|---|---|---|---|
| 2005/0165306 A1* | 7/2005 | Zheng | A61B 8/485 600/437 |
| 2008/0281196 A1* | 11/2008 | Sornes | A61B 5/02007 600/437 |
| 2010/0016718 A1* | 1/2010 | Fan | A61B 8/00 600/438 |
| 2010/0168566 A1* | 7/2010 | Bercoff | A61B 8/08 600/438 |
| 2012/0089019 A1* | 4/2012 | Fan | A61B 8/485 600/437 |
| 2013/0218011 A1* | 8/2013 | Benson | A61B 8/463 600/438 |
| 2014/0088423 A1 | 3/2014 | Noguchi et al. | |
| 2014/0288425 A1 | 9/2014 | Shin et al. | |
| 2015/0080730 A1* | 3/2015 | Kanayama | A61B 8/5207 600/447 |
| 2015/0094579 A1* | 4/2015 | Fan | A61B 8/085 600/438 |
| 2015/0133782 A1* | 5/2015 | Yoshikawa | A61B 8/485 600/438 |
| 2015/0148673 A1* | 5/2015 | Yoshikawa | A61B 8/5223 600/438 |
| 2015/0164476 A1* | 6/2015 | Kong | A61B 8/485 600/438 |
| 2015/0164480 A1* | 6/2015 | Watanabe | A61B 8/463 600/438 |
| 2015/0173718 A1* | 6/2015 | Tabaru | A61B 8/08 600/438 |
| 2016/0143621 A1* | 5/2016 | Parthasarathy | A61B 8/085 600/438 |
| 2016/0143622 A1* | 5/2016 | Xie | A61B 8/4245 600/424 |
| 2016/0183926 A1* | 6/2016 | Asami | A61B 8/485 600/438 |

FOREIGN PATENT DOCUMENTS

| | | |
|---|---|---|
| CN | 104302233 A | 1/2015 |
| EP | 1 629 777 A1 | 3/2006 |
| EP | 2 497 425 A1 | 9/2012 |
| EP | 2 599 443 A1 | 6/2013 |
| EP | 2 716 232 A1 | 4/2014 |
| EP | 3 040 033 A1 | 7/2016 |
| JP | 2007-6914 A | 1/2007 |
| KR | 1020140115921 A | 10/2014 |
| WO | 2014136502 A1 | 9/2014 |
| WO | 2015029651 A1 | 3/2015 |

OTHER PUBLICATIONS

Communication dated Mar. 27, 2018, issued by the Korean Intellectual Property Office in corresponding Korean Application No. 10-2015-0115415.

Communication dated May 4, 2018, from the State Intellectual Property Office of People's Republic of China in counterpart Application No. 201610191654.6.

* cited by examiner

ULTRASOUND IMAGING APPARATUS AND METHOD OF PROCESSING ULTRASOUND IMAGE THEREOF

CROSS-REFERENCE TO RELATED APPLICATIONS

This application claims priority from Korean Patent Application No. 10-2015-0045331, filed on Mar. 31, 2015, and from Korean Patent Application No. 10-2015-0115415, filed on Aug. 17, 2015, in the Korean Intellectual Property Office, the disclosures of which are incorporated herein by reference in their respective entireties.

BACKGROUND

1. Field

Exemplary embodiments relate to ultrasound imaging apparatuses and methods for processing an ultrasound image thereof.

2. Description of the Related Art

An ultrasound imaging apparatus obtains at least one image that relates to an inner portion (for example, a soft tissue or blood flow) of an object by irradiating an ultrasound signal generated by a transducer of a probe toward the object, and receiving information of an echo signal reflected by the object. In particular, the ultrasound imaging apparatus is usable for a medical purpose, such as observation of the inside of the object, foreign substance detection, and injury measurement. Compared with a diagnosis apparatus that uses an X-ray, the ultrasound imaging apparatus has high stability, may display an image in real-time, and has an advantage of being relatively safe because there is no exposure to radiation. Therefore, an ultrasound imaging apparatus is widely used together with other imaging apparatuses including a computed tomography (CT) apparatus, a magnetic resonance imaging (MRI) apparatus, and other suitable apparatuses.

The ultrasound imaging apparatus may calculate an elasticity value, which is a value that represents the elasticity of an object, and provide the same to a user. The elasticity of an object is related to a pathological phenomenon of the object. When an ultrasound imaging apparatus provides an elasticity value to a user, the user needs to know whether the elasticity value provided to the user is an accurate value. U.S. Patent Publication No. 2013/02118011 A1 discloses a construction of providing the quality of a shear wave to a user by using a signal-to-noise ratio (SNR) and other relevant parameters of the shear wave. However, even when the quality (for example, an SNR) of the shear wave is good, a calculated elasticity value may not be a reliable value. In addition, it is difficult for a user to intuitively determine whether an elasticity value provided to the user is a reliable value based solely on the quality of a shear wave.

SUMMARY

Provided are methods and ultrasound imaging apparatuses for providing an elasticity value to a user.

Provided are ultrasound imaging apparatuses and methods for processing an ultrasound image thereof, that enable a user to more accurately and intuitively recognize whether an obtained elasticity value is a reliable value.

Additional aspects will be set forth in part in the description which follows and, in part, will be apparent from the description, or may be learned by practice of the presented exemplary embodiments.

According to an aspect of an exemplary embodiment, a method for processing an ultrasound image in which an ultrasound imaging apparatus provides an elasticity value is provided. The method includes: inducing a shear wave inside an object; obtaining an elasticity value that relates to the object based on the induced shear wave; determining a reliability value that relates to the obtained elasticity value based on a result of a comparison of the obtained elasticity value with a reference value that corresponds to the induced shear wave; and displaying a user interface screen that includes a respective representation of each of the obtained elasticity value and the determined reliability value.

The determining the reliability value may include: determining the reliability value based on a result of a comparison between a magnitude of the induced shear wave and the obtained elasticity value and the reference value.

The determining the reliability value may include: obtaining a residual value that corresponds to a difference between the obtained elasticity value and the reference value; and determining the reliability value based on a magnitude of the determined shear wave and the obtained residual value.

The determining the reliability value may include: when the shear wave is applied to a wave equation, obtaining a residual value that corresponds to an error of the shear wave with respect to the wave equation; and determining the reliability value based on a magnitude of the induced shear wave and the obtained residual value.

The obtaining the elasticity value may include: determining a magnitude of the induced shear wave and using the determined magnitude as the elasticity value, wherein the determining the reliability value may include: calculating a first numerical value based on the determined magnitude of the shear wave; calculating a second numerical value based on a result of the comparison; and determining the reliability value based on the calculated first numerical value and the calculated second numerical value.

The calculating the second numerical value may include: calculating the second numerical value based on a residual value that corresponds to a difference between the obtained elasticity value and the reference value.

The determined reliability value may be equal to or greater than zero and equal to or less than one.

The displaying may include: displaying the representation of the reliability value by using a numerical value.

The displaying may include: displaying a graph that indicates a magnitude of the determined reliability value.

The displaying may include: displaying the representation of the obtained elasticity value by using a color that corresponds to a magnitude of the determined reliability value.

The displaying may include: displaying at least one from among an image, a letter, an icon, and a symbol that corresponds to a magnitude of the determined reliability value.

The displaying may include: displaying a screen which includes an ultrasound image that includes a respective representation of each of the object, the obtained elasticity value, and the determined reliability value.

The displaying may include: displaying a screen which includes an elasticity image generated based on the induced shear wave, the obtained elasticity value, and the determined reliability value.

The method may further include: setting a region of interest (ROI) with respect to the object, wherein the obtaining the elasticity value may include: obtaining an elasticity value that relates to the object inside the region of interest based on an observation of the induced shear wave with respect to an inside of the ROI.

The method may further include: determining a quality of the induced shear wave, wherein the displaying may include: displaying a user interface screen which includes a respective representation of each of the obtained elasticity value, the determined reliability value, and the determined quality.

According to an aspect of another exemplary embodiment, a method for processing an ultrasound image in which an ultrasound imaging apparatus provides an elasticity value is provided. The method includes: obtaining an elasticity value for an object based on ultrasound data obtained by observing a shear wave that is induced with respect to the object; determining a reliability value that relates to the obtained elasticity value based on a result of a comparison of the obtained elasticity value with a reference value that corresponds to the induced shear wave; and displaying a user interface screen that includes a respective representation of each of the obtained elasticity value and the determined reliability value.

According to an aspect of another exemplary embodiment, an ultrasound imaging apparatus includes: a controller configured to obtain an elasticity value that relates to an object based on a shear wave induced inside the object, and to determine a reliability value that relates to the obtained elasticity value based on a result of a comparison of the obtained elasticity value with a reference value that corresponds to the induced shear wave; and a display configured to display a user interface screen that includes a respective representation of each of the obtained elasticity value and the determined reliability value.

The controller may be further configured to determine the reliability value based on a result of a comparison between a magnitude of the induced shear wave and the obtained elasticity value and the reference value.

The controller may be further configured to obtain a residual value that corresponds to a difference between the obtained elasticity value and the determined reference value, and to determine the reliability value based on a magnitude of the induced shear wave and the obtained residual value.

The controller may be further configured to obtain a residual value that corresponds to an error of the shear wave with respect to a wave equation when the shear wave is applied to the wave equation, and to determine the reliability value based on a magnitude of the induced shear wave and the obtained residual value.

The controller may be further configured to determine a magnitude of the induced shear wave and to use the determined magnitude as the elasticity value, to calculate a first numerical value based on the determined magnitude of the shear wave, to calculate a second numerical value based on a result of the comparison, and to determine the reliability value based on the calculated first numerical value and the calculated second numerical value.

The controller may be further configured to calculate the second numerical value based on a residual value that corresponds to a difference between the obtained elasticity value and the reference value.

The reliability value may be equal to or greater than zero and equal to or less than one.

The ultrasound imaging apparatus may further include: an ultrasound transceiver configured to induce the shear wave inside the object, and to observe the induced shear wave.

The ultrasound imaging apparatus may further include: a communication module configured to receive the induced shear wave from a wireless probe.

The display may be further configured to display the representation of the determined reliability value by using a numerical value.

The display may be further configured to display a graph which indicates a magnitude of the determined reliability value.

The display may be further configured to display the representation of the obtained elasticity value by using a color that corresponds to a magnitude of the determined reliability value.

The display may be further configured to display at least one from among an image, a letter, an icon, and a symbol that corresponds to a magnitude of the determined reliability value.

The controller may be further configured to determine a quality of the induced shear wave based on a displacement characteristic of the shear wave.

The display may be further configured to display a user interface screen which includes a respective representation of each of the obtained elasticity value, the determined reliability value, and the determined quality.

A non-transitory recording medium according to an exemplary embodiment may be a non-transitory computer-readable recoding medium having recorded thereon a program that is executable for performing the above-described method for processing an ultrasound image.

BRIEF DESCRIPTION OF THE DRAWINGS

Exemplary embodiments will now be described more fully hereinafter with reference to the accompanying drawings, in which reference numerals denote structural elements.

DETAILED DESCRIPTION

Figure 1:
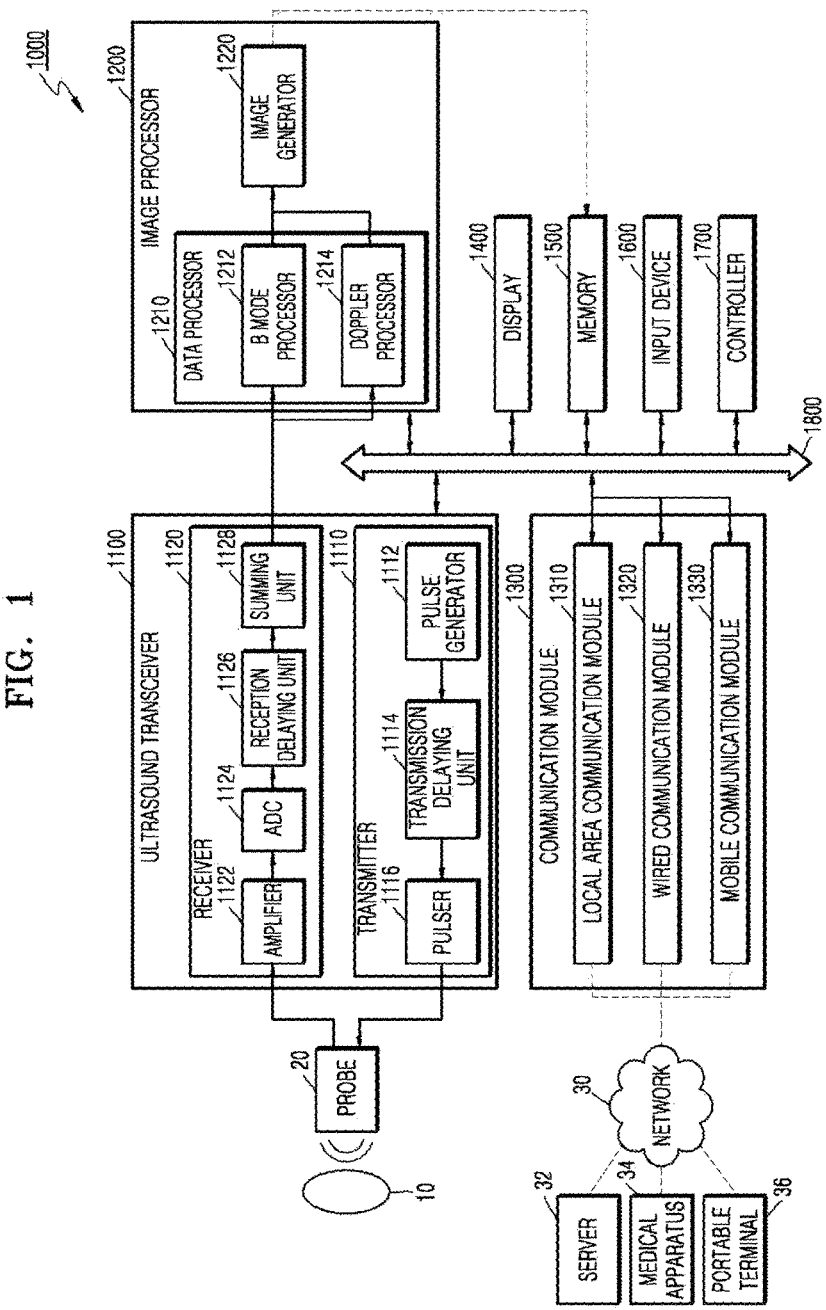
FIG. 1 is a block diagram illustrating a configuration of an ultrasound diagnosis apparatus, according to an exemplary embodiment.

Exemplary embodiments are described in detail with reference to the accompanying drawings so as to enable a person of ordinary skill in the art to easily implement the present inventive concept. In this regard, the present exemplary embodiments may have different forms and should not be construed as being limited to the descriptions set forth herein. Further, for clarity, portions irrelevant to the description are omitted from the drawings, and like reference numerals are used for like components throughout the specification.

The terms used in this specification are those general terms currently widely used in the art in consideration of functions that relate to the exemplary embodiments, but the terms may vary according to the intention of those of ordinary skill in the art, precedents, or new technology in the art. Further, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the exemplary embodiments.

It will be understood that when a certain portion is referred to as being "connected" to another portion, it may be "directly connected" to the other portion or may be "electrically connected" to the other portion with other device interposed therebetween. When a part "includes" or "comprises" an element, unless there is a particular description contrary thereto, the part can further include other elements, not excluding the other elements.

Throughout the specification, an "ultrasound image" refers to an image of an object, which is obtained by using ultrasound waves. Furthermore, an "object" may be any of a human, an animal, or a part of a human or animal. For example, the object may be an organ (e.g., the liver, heart, womb, brain, breast, or abdomen), a blood vessel, or a combination thereof. Further, the object may be a phantom.

The phantom refers to a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Throughout the specification, an "elasticity value" denotes a value representing a degree of elasticity held by a tissue of an object. Further, a "reliability value" that relates to the elasticity value denotes a value representing a degree to which the elasticity value calculated by an ultrasound imaging apparatus is reliable. The "reliability value" may be referred to as a reliable measurement index or a measure reliability index. In addition, a residual value may denote a difference between a value obtained from an observed value or a measurement value for an elasticity value, and a calculated value or a theoretical value. Exemplary embodiments are described below with reference to the accompanying drawings.

FIG. 1 is a block diagram showing a configuration of an ultrasound diagnosis apparatus 1000, according to an exemplary embodiment. Referring to FIG. 1, the ultrasound diagnosis apparatus 1000 may include a probe 20, an ultrasound transceiver 1100, an image processor 1200, a communication module 1300, a display 1400, a memory 1500, an input device 1600, and a controller 1700, all of which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet personal computer (PC).

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to exemplary embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit (also referred to herein as a "transmission delayer") 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing that corresponds to each of the pulses which have been delayed.

A receiver 1120 generates ultrasound data by processing echo signals received from the probe 20. The receiver 1120 may include an amplifier 1122, an analog-to-digital converter (ADC) 1124, a reception delaying unit (also referred to herein as a "reception delayer") 1126, and a summing unit (also referred to herein as a "summer" or an "adder") 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some exemplary embodiments, the receiver 1120 may not include the amplifier 1122. In this aspect, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may include not only a grayscale ultrasound image obtained by scanning an object in an amplitude (A) mode, a brightness (B) mode, and a motion (M) mode, but also a Doppler image which illustrates a movement of an object via a Doppler effect. The Doppler image may be any of a blood flow Doppler image that shows flow of blood (also referred to as a color Doppler image), a tissue Doppler image that shows a movement of tissue, or a spectral Doppler image that shows a moving speed of an object as a waveform.

A B mode processor 1212 included in a data processor 1210 extracts a B mode component from ultrasound data and processes the extracted B mode component. An image generator 1220 may generate an ultrasound image which indicates signal intensities as brightnesses based on the extracted B mode components 1212.

Likewise, a Doppler processor 1214 included in the data processor 1210 may extract a Doppler component from ultrasound data, and the image generator 1220 may generate a Doppler image which expresses a movement of an object in a color or a waveform based on the extracted Doppler component.

According to an exemplary embodiment, the image generator 1220 may generate a three-dimensional (3D) ultrasound image via volume-rendering with respect to volume data and may also generate an elasticity image by imaging a deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to exemplary embodiments.

The communication module 1300 is connected to a network 30 by wire or wirelessly in order to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data which relates to a diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information which relates to a diagnosis history or medical treatment schedule of a patient from a server and may utilize the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly in order to exchange data with a server 32, a medical apparatus 34, or a portable terminal 36. The communication module 1300 may include one or more components which are configured for facilitating communication with external devices. For example, the communication module 1300 may include a local area communication module 1310, a wired communication module 1320, and a mobile communication module 1330.

The local area communication module 1310 refers to a module configured for performing local area communication within a predetermined distance. Examples of local area communication technology according to an exemplary embodiment include, but are not limited to, a wireless local area network (LAN), Wi-Fi, Bluetooth, ZigBee, Wi-Fi direct (WFD), ultra wideband (UWB), infrared data association (IrDA), Bluetooth low energy (BLE), and near field communication (NFC).

The wired communication module 1320 refers to a module configured for performing communication by using electric signals or optical signals. Examples of wired communication techniques according to an exemplary embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may include voice call signals, video call signals, and/or various types of data for transmission and reception of text/multimedia messages.

The memory 1500 stores various data processed by the ultrasound diagnosis apparatus 1000. For example, the memory 1500 may store medical data that relates to a diagnosis of an object, such as ultrasound data and an ultrasound image that are input or output, and may also store algorithms or programs which are to be executed in the ultrasound diagnosis apparatus 1000.

The memory 1500 may include any of various storage media, e.g., a flash memory, a hard disk drive, EEPROM, and/or any other suitable type of storage medium. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as any of a keypad, a mouse, a touch pad, a touch screen, and a jog switch. However, exemplary embodiments are not limited thereto, and the input device 1600 may further include any of various other input units such as, for example, an electrocardiogram (ECG) measuring module, a respiration measuring module, a voice recognition sensor, a gesture recognition sensor, a fingerprint recognition sensor, an iris recognition sensor, a depth sensor, a distance sensor, and/or any other suitable type of input device.

The controller 1700 may control all operations of the ultrasound diagnosis apparatus 1000. In particular, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. Furthermore, at least one selected from the ultrasound transceiver 1100, the image processor 1200, and the communication module 1300 may be included in the controller 1600. However, exemplary embodiments are not limited thereto.

Figure 2:
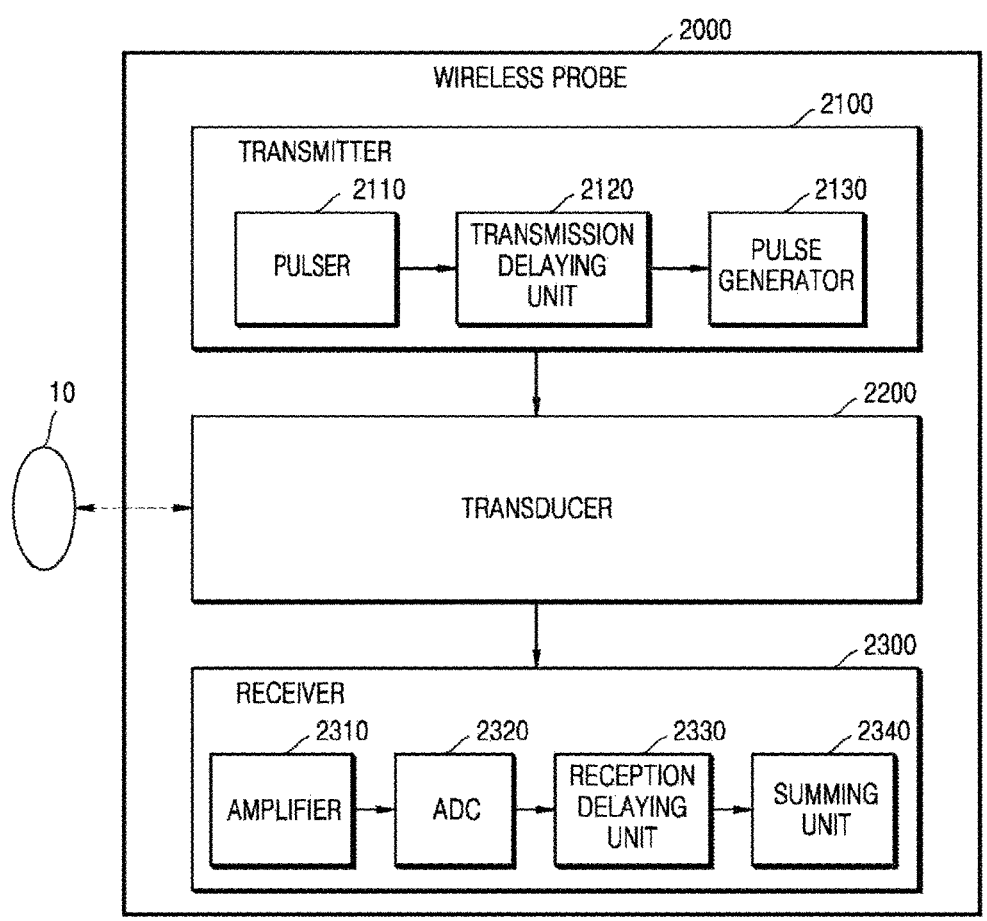
FIG. 2 is a block diagram illustrating a configuration of a wireless probe, according to an exemplary embodiment.

FIG. 2 is a block diagram showing a configuration of a wireless probe 2000, according to an exemplary embodiment. As described above with reference to FIG. 1, the wireless probe 2000 may include a plurality of transducers, and, according to exemplary embodiments, may include some or all of the components of the ultrasound transceiver 100 shown in FIG. 1.

The wireless probe 2000 according to the exemplary embodiment shown in FIG. 2 includes a transmitter 2100, a transducer 2200, and a receiver 2300. Since descriptions thereof are provided above with reference to FIG. 1, detailed descriptions thereof will be omitted here. In addition, according to exemplary embodiments, the wireless probe 2000 may selectively include a reception delaying unit (also referred to herein as a "reception delayer") 2330 and a summing unit (also referred to herein as a "summer" and/or as an "adder") 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

An ultrasound imaging apparatus that enables a user to intuitively recognize whether an obtained elasticity value is a reliable value according to an exemplary embodiment is described below with reference to FIGS. 3A to 20.

The ultrasound imaging apparatus according to an exemplary embodiment may include any medical imaging apparatus that is configured to obtain ultrasound data, and to obtain and process an elasticity value based on the obtained ultrasound data. In particular, the ultrasound imaging apparatus according to an exemplary embodiment may correspond to the ultrasound imaging apparatus 1000 illustrated in FIG. 1. Further, the ultrasound imaging apparatus according to an exemplary embodiment may include a medical imaging apparatus that transmits/receives data to/from a wireless probe illustrated in FIG. 2 via a wireless network. In particular, the ultrasound imaging apparatus according to an exemplary embodiment may include any medical imaging apparatus that is configured to obtain and process an elasticity value by using ultrasound data received from the wireless probe illustrated in FIG. 2.

Figure 3A:
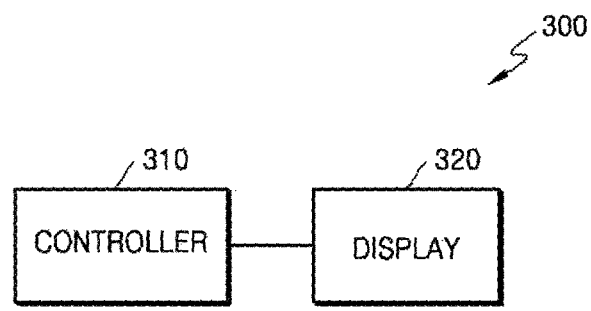
FIG. 3A is a block diagram illustrating a configuration of an ultrasound imaging apparatus, according to an exemplary embodiment.

FIG. 3A is a block diagram illustrating a configuration of an ultrasound imaging apparatus 300, according to an exemplary embodiment.

The ultrasound imaging apparatus 300 according to an exemplary embodiment may include a controller 310 and a display 320. The controller 310 and the display 320 of FIG. 3A may correspond to the controller 1700 and the display 1400 of FIG. 1, respectively. In particular, the ultrasound imaging apparatus 300 may be included in or equivalently correspond to the ultrasound imaging apparatus 1000 illustrated in FIG. 1.

The controller 310 according to an exemplary embodiment may control each component of the ultrasound imaging apparatus 300. The controller 310 may obtain an elasticity value of an object by controlling each component of the ultrasound imaging apparatus 300. A method for obtaining an elasticity value may be implemented in any of various ways based on an exemplary embodiment.

According to an exemplary embodiment, an elasticity value may denote a modulus of elasticity. For example, an elasticity value is a value that represents a degree of transformation of an object to which a shear wave has been induced, and may be expressed as a shear modulus of elasticity, a Young's modulus, a shear velocity value, an/or any other suitable type of value.

In the case in which the ultrasound imaging apparatus 300 equivalently corresponds to the ultrasound imaging apparatus 1000 illustrated in FIG. 1, the ultrasound imaging apparatus 300 may further include some or all of internal components of the ultrasound imaging apparatus 1000, in addition to the inclusions of the controller 310 and the display 320. For example, the ultrasound imaging apparatus 300 may further include the transceiver 1100 and the probe 20 of FIG. 1.

The controller 310 may be configured to obtain ultrasound data by tracking and/or observing a shear wave induced to an object 10, and to obtain an elasticity value of the object 10 based on the obtained ultrasound data. In particular, the obtained ultrasound data is ultrasound data which is obtainable by tracking and/or observing a shear wave induced to the object 10, and which may be self-obtained by using a probe provided inside the ultrasound imaging apparatus 300 and/or which may be received from outside.

According to an exemplary embodiment, the controller 310 may induce a shear wave to the object 10 by using the ultrasound transceiver 1100 and the probe 20 of FIG. 1. Further, the controller 310 may observe the induced shear wave and obtain an elasticity value of the object 10 based on the observation of the shear wave.

According to an exemplary embodiment, the controller 310 may obtain an elasticity value of the object 10 based on a velocity of a shear wave included in elasticity data which is obtained by tracking the induced shear wave by using the ultrasound transceiver 1100 and the probe 20. In this aspect, the elasticity value may be an elasticity value of an object inside a region of interest set for an ultrasound image. For another example, the controller 310 may obtain an elasticity value stored in the memory 1500 of FIG. 1. For another example, the controller 310 may receive information which includes an elasticity value from other devices by using the communication module 1300. However, the exemplary embodiment is not limited thereto.

In addition, the controller 310 may be configured to determine a reliability value that relates to an obtained elasticity value. According to an exemplary embodiment, the controller 310 may calculate a reliability value based on information related to an elasticity value. According to an exemplary embodiment, the controller 310 may determine a reliability value for an obtained elasticity value based on a result of a comparison between the obtained elasticity value and a reference value that corresponds to an induced shear wave.

As described above, the "reliability value" for the elasticity value denotes a value which represents a degree to which the elasticity value calculated by the ultrasound imaging apparatus is reliable.

For example, when a shear wave is applied to a wave equation, the "reliability value" may be a value which represents a degree to which the shear wave matches the wave equation. An elasticity value may be calculated by inducing a shear wave to an object and using the induced shear wave. A reliability value may be a statistical value of theoretical differences between an elasticity value calculated by using an induced shear wave and an induced shear wave. In particular, the "theoretical difference" may denote a residual value which remains after an elasticity value and an observed shear wave are input into a wave equation. Further, the "statistical value of the theoretical differences" may denote a value calculated by using a sum of the theoretical differences.

For example, the controller 310 may calculate a reliability value based on a magnitude of a shear wave and a residual value obtained during a process of calculating an elasticity value. In this aspect, the controller 310 may determine a relatively high reliability value when a magnitude of a shear wave is large, and determine a relatively high reliability value when a residual value is small.

A residual value may be a value obtained based on a result of a comparison between an obtained elasticity value and a reference value that corresponds to an induced shear wave.

A residual value may be defined by using any of various methods based on an exemplary embodiment. For example, a residual value may be defined by Equation 1 below based on a wave equation.

$$res = \sum \left| \frac{\partial^2 u}{\partial t^2} - c^2 \nabla^2 u \right|^2 \quad \text{Equation 1}$$

In Equation 1, the right side is an expression that represents a wave equation, and a value of the right side becomes equal to zero when a waveform completely matches a wave equation. However, an error included in a transverse wave may appear due to an environment that relates to observing a shear wave, an environment that relates to inducing a shear wave, and/or based on other factors, so that a value of the left side may not be equal to zero.

In Equation 1, the left side (res) represents a residual value, and the residual value may be a value that corresponds to an error of a transverse wave which appears in an application of the above-described wave equation. In particular, Equation 1 may be a value that represents a difference between an obtained elasticity value and a reference value that corresponds to an induced shear wave.

Alternatively, a residual value may be also defined by Equation 2 below based on a Voigt model.

$$res = \sum \left| \frac{\partial^2 u}{\partial t^2} - \left( c^2 + \frac{\eta}{\rho} \frac{\partial}{\partial t} \right) \nabla^2 u \right|^2 \quad \text{Equation 2}$$

In Equation 2, $$\nabla^2 u = \frac{\partial^2 u}{\partial x^2} + \frac{\partial^2 u}{\partial y^2} + \frac{\partial^2 u}{\partial z^2}$$

$$\nabla^2 u = \frac{1}{r} \frac{\partial}{\partial r} \left( r \frac{\partial u}{\partial r} \right) + \frac{1}{r^2} \frac{\partial^2 u}{\partial \theta^2}$$

$$\nabla^2 u = \frac{1}{r} \frac{\partial}{\partial r} \left( r \frac{\partial u}{\partial r} \right) + \frac{1}{r^2} \frac{\partial^2 u}{\partial \varphi^2} + \frac{\partial^2 u}{\partial z^2}$$

In this aspect, since the above equation is based on a three-dimensional (3D) image, some terms may not be calculable based on a two-dimensional (2D) ultrasound image. According to an exemplary embodiment, a value that may not be calculable based on a 2D ultrasound image may be processed as being equal to zero.

Further, according to an exemplary embodiment, a residual value may denote a normalized value as expressed in Equation 3.

$$res_n = \frac{res}{\sum |\nabla^2 u|^2} \quad \text{Equation 3}$$

or $$res_n = \frac{res}{\sum \left| \frac{\partial^2 u}{\partial t^2} \right|^2}$$

In Equations 1, 2, and 3, "u" denotes a particle displacement of an observed shear wave or a particle velocity, "c" denotes a transfer velocity of a shear wave, "η" denotes the viscosity of an object, and "ρ" denotes the density of an object.

For another example, a residual value may be also defined by Equation 4 based on a time-to-peak method.

$$res = \sum_i |c \cdot x_i - t_i|^2 \quad \text{Equation 4}$$

In Equation 4, $t_i$ denotes an arrival time of an i-th peak, and $x_i$ denotes a lateral distance of an i-th peak.

As described in Equations 1, 2, 3, and 4, a residual value may be a value which represents a difference between an obtained elasticity value and a reference value that corresponds to an induced shear wave. In particular, the "reference value that corresponds to the induced shear wave" may be an ideal elasticity value of a shear wave as applied to a wave equation.

The display 320 may display a user interface screen that includes a respective representation of each of an obtained elasticity value and a reliability value. In particular, a method for displaying an elasticity value and a reliability value may vary based on an exemplary embodiment. According to an exemplary embodiment, the display 320 may display each of an elasticity value and a reliability value as a respective numerical value. In this aspect, the reliability value may be equal to or greater than zero (0) and equal to or less than one (1). According to an exemplary embodiment, the display 320 may display a graph that represents a magnitude of a reliability value. Further, according to an exemplary embodiment, the display 320 may display an elasticity value by using a color that corresponds to a magnitude of a reliability value. As described above, when a reliability value is equal to or greater than about 0.7, the display 320 may display an elasticity value as a green letter, and when a reliability value is less than about 0.7, the display 320 may display an elasticity value as a red letter.

Alternatively, the display 320 may display at least one from among an image, a letter, an icon, and a symbol that corresponds to a magnitude of a reliability value. Alternatively, the display 320 may display an elasticity value and a reliability value by using a combination of the above exemplary embodiments.

Figure 3B:
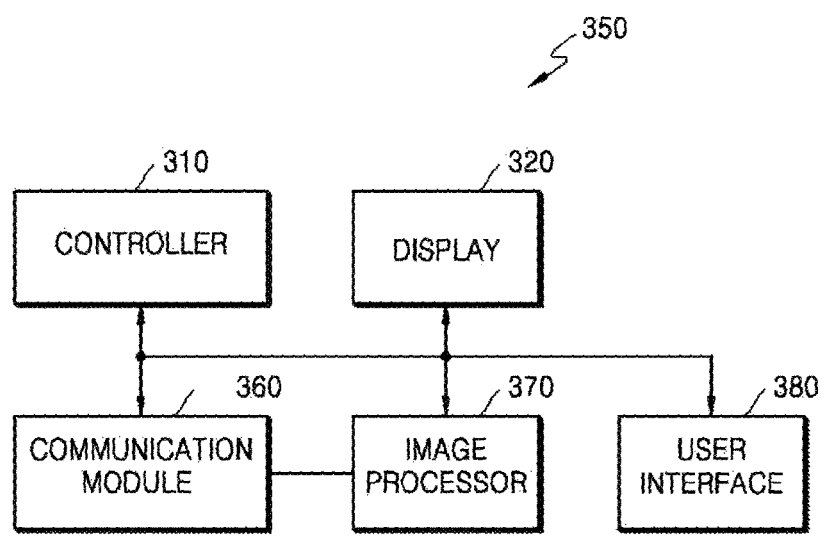
FIG. 3B is a block diagram illustrating a configuration of an ultrasound imaging apparatus, according to another exemplary embodiment.

FIG. 3B is a block diagram illustrating a configuration of an ultrasound imaging apparatus 350, according to another exemplary embodiment. The same components of the ultrasound imaging apparatus 350 as those of the ultrasound imaging apparatus 300 illustrated in FIG. 3A are denoted by using the same reference numerals.

Compared with the ultrasound imaging apparatus 300, the ultrasound imaging apparatus 350 may further include at least one of a communication module 360, an image processor 370, and a user interface 380.

The communication module 360 may transmit/receive data to/from at least one of an external server, a medical apparatus, and a portable terminal via a wired/wireless communication network. According to an exemplary embodiment, the communication module 360 may equivalently correspond to the communication module 1300 of FIG. 1.

The ultrasound imaging apparatus 350 may be configured to receive ultrasound data for obtaining an elasticity value of an object from an external medical apparatus, such as, for example, a wireless probe (not shown), and to obtain an elasticity value based on the received ultrasound data. In this case, the communication module 360 may receive ultrasound data from the wireless probe (not shown) via a wireless network.

According to an exemplary embodiment, the controller 310 may control to facilitate an inducement of a shear wave to the object 10 via the externally connected wireless probe (not shown). Further, when the wireless probe (not shown) observes the induced shear wave, obtains corresponding ultrasound data, and transmits the obtained ultrasound data to the ultrasound imaging apparatus 350, the controller 310 may obtain an elasticity value of the object based on the ultrasound data that represents the observation of the induced shear wave.

In addition, the controller 310 may determine a reliability value for an obtained elasticity value. According to an exemplary embodiment, the controller 310 may calculate a reliability value based on information that relates to an elasticity value.

The display 320 may display a user interface screen that includes a respective representation of each of an obtained elasticity value and a reliability value.

The image processor 370 may generate an ultrasound image based on ultrasound data that corresponds to an ultrasound echo signal received from the wireless probe 2000 (see FIG. 2) or the probe 10 (see FIG. 1). The image processor 370 may equivalently correspond to the image processor 1200 of FIG. 1. According to an exemplary embodiment, an ultrasound image generated by the image processor 370 may include not only an image of a gray scale obtained by scanning an object under an A mode, a B mode, and an M mode, but also a Doppler image that illustrates a moving object by using a Doppler effect. Further, an ultrasound image generated by the image processor 370 may include an elasticity image that is generated based on ultrasound data.

The display 320 may display an ultrasound image generated by the image processor 370. According to an exemplary embodiment, the display 320 may display a user interface screen that includes each of an ultrasound image, an elasticity value obtained by the controller 310, and a reliability value that relates to the obtained elasticity value. For example, the display 320 may display a user interface screen that includes each of an ultrasound image in which an elasticity image overlaps on a portion, for example, an ROI of a B mode ultrasound image, an elasticity value obtained by the controller 310, and a reliability value for the obtained elasticity value.

The user interface 380 is configured for receiving a predetermined instruction and/or data from a user. The user interface 380 may correspond to the input device 1600 of FIG. 1.

According to an exemplary embodiment, the user interface 380 may generate and output a user interface screen for receiving a predetermined instruction and/or data from a user. Further, the user interface 380 may receive a predetermined instruction and/or data from a user via the user interface screen. A user may recognize predetermined information by viewing the user interface screen displayed via the display 320, and input a predetermined instruction or data via the user interface 380.

According to an exemplary embodiment, the user interface 380 may receive a user input for setting a region of interest (ROI), and set a predetermined region of an ultrasound image as an ROI according to the received user input.

An operation of an ultrasound imaging apparatus according to an exemplary embodiment is described below with reference to the ultrasound imaging apparatus illustrated in FIG. 3B.

Figure 4:
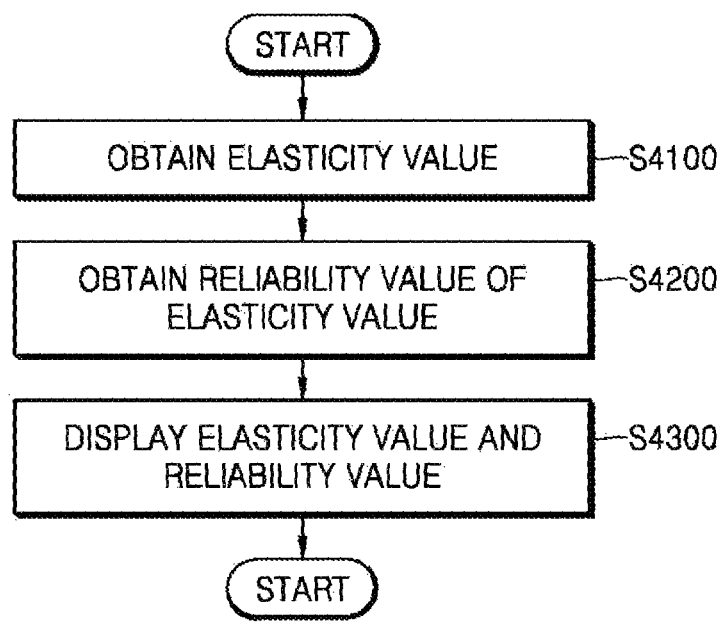
FIG. 4 is a flowchart illustrating a process for providing an elasticity value, according to an exemplary embodiment.

FIG. 4 is a flowchart illustrating a process for providing an elasticity value, according to an exemplary embodiment.

In operation S4100, the ultrasound imaging apparatus 350 may obtain an elasticity value of an object. A method for obtaining an elasticity value may be implemented in any of various ways based on an exemplary embodiment. For example, the ultrasound imaging apparatus 350 may induce a shear wave to the object 10 by using the ultrasound transceiver 1100 and the probe 20 of FIG. 1. Further, the ultrasound imaging apparatus 350 may obtain an elasticity value of the object 10 based on a velocity of a shear wave included in elasticity data obtained by tracking the shear wave induced by using the ultrasound transceiver 1100 and the probe 20. For another example, the ultrasound imaging apparatus 350 may receive information which includes an elasticity value from other devices by using the communication module 360, but is not limited thereto.

Then, in operation S4200, the ultrasound imaging apparatus 350 may determine a reliability value that relates to the obtained elasticity value. According to an exemplary embodiment, the ultrasound imaging apparatus 350 may calculate a reliability value based on information that relates to an elasticity value. For example, the ultrasound imaging apparatus 350 may calculate a reliability value based on a magnitude of a shear wave and a residual value obtained during a process of calculating an elasticity value. In particular, the ultrasound imaging apparatus 350 may determine a relatively high reliability value when a magnitude of a shear wave is large, and determine a relatively high reliability value when a residual value is small.

Then, in operation S4300, the ultrasound imaging apparatus 350 may display a respective representation of each of an elasticity value and a reliability value via the display 320. In this aspect, a method for displaying the elasticity value and the reliability value may vary based on an exemplary embodiment. According to an exemplary embodiment, the display 320 may display each of an elasticity value and a reliability value as a respective numerical value. In particular, the reliability value may be equal to or greater than 0 and equal to or less than 1. According to an exemplary embodiment, the display 320 may display a graph that represents a magnitude of a reliability value. Further, according to an exemplary embodiment, the display 320 may display a representation of an elasticity value by using a color that corresponds to a magnitude of a reliability value. For example, when a reliability value is equal to or greater than about 0.7, the display 320 may display an elasticity value as a green letter, and when a reliability value is less than about 0.7, the display 320 may display an elasticity value as a red letter. Alternatively, the display 320 may display at least one from among an image, a letter, an icon, and a symbol that corresponds to a magnitude of a reliability value. Alternatively, the display 320 may display an elasticity value and a reliability value by using a combination of the above exemplary embodiments.

Figure 5:
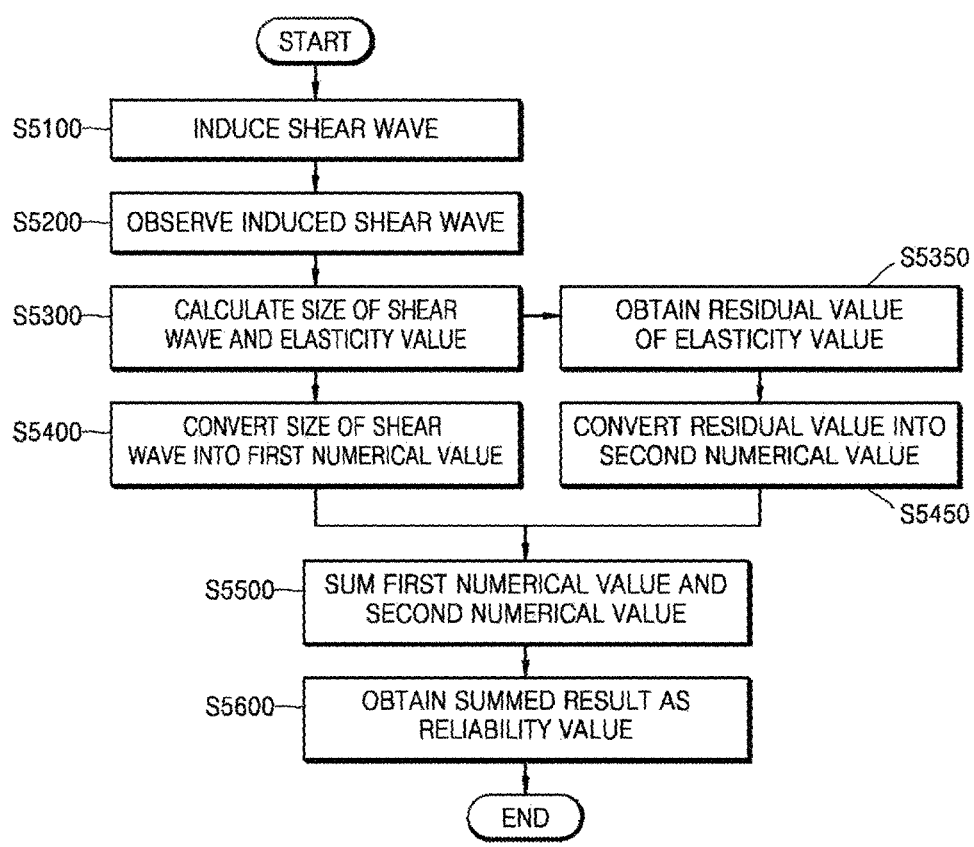
FIG. 5 is a flowchart illustrating a process for providing a reliability value, according to an exemplary embodiment.

FIG. 5 is a flowchart illustrating a process for obtaining a reliability value, according to an exemplary embodiment.

In operation S5100, the ultrasound imaging apparatus 350 may induce a shear wave inside an object. The ultrasound imaging apparatus 350 may facilitate the generation of a shear wave inside the object by transmitting an ultrasound wave that pushes a tissue inside the object. Then, in operation S5200, the ultrasound imaging apparatus 350 may track the induced shear wave. The ultrasound imaging apparatus 350 may calculate a velocity of the tracked shear wave.

In operation S5300, the ultrasound imaging apparatus 350 may calculate a magnitude (i.e., an amplitude) of the induced shear wave and an elasticity value based on observations obtained in operation S5200. Generally, the velocity of a shear wave is proportional to elasticity. In this aspect, the ultrasound imaging apparatus 350 may calculate an elasticity value based on the velocity of a shear wave. Further, the ultrasound imaging apparatus 350 may obtain a residual value that relates to the obtained elasticity value in operation S5350. A residual value may be obtained by using any of various methods based on an exemplary embodiment.

Then, in operation S5400, the ultrasound imaging apparatus 350 may convert the determined magnitude of the shear wave into a first numerical value. In particular, the first numerical value denotes a value which represents the reliability of an elasticity value as determined based on a magnitude of a shear wave. Generally, since the reliability of an elasticity value is relatively high when a magnitude of a shear wave is large, the ultrasound imaging apparatus 350 may determine the first numerical value based on a magnitude of a shear wave. The first numerical value may be defined by Equation 5 below.

$$\text{score}_u = \left(\frac{a}{u_{max} - u_{min}}\right)u - \left(\frac{a \cdot u_{min}}{u_{max} \cdot u_{min}}\right), \quad \text{Equation 5}$$

$$(0 \leq a \leq 1)$$

In Equation 5, $\text{score}_u$ is a first numerical value, "u" is a size (i.e., magnitude or amplitude) of a transverse wave, and $u_{max}$ and $u_{min}$ denote values set in advance for obtaining the first numerical value. Further, "a" may represent a maximum value according to a weight for the first numerical value from among reliability values. For example, the first numerical value may be equal to or greater than 0 and equal to or less than "a".

In addition, the ultrasound imaging apparatus 350 may convert a residual value into a second numerical value in operation S5450. In particular, the second numerical value denotes the reliability of an elasticity value as determined based on a residual value. Generally, since the reliability of an elasticity value is relatively high when a residual value is small, the ultrasound imaging apparatus 350 may determine the second numerical value based on a residual value. The second numerical value may be defined by Equation 6 below.

$$\text{score}_{res} = -\left(\frac{b}{res_n - res_n}\right)res - \left(\frac{b \cdot res_{min}}{res_{max} - res_{min}}\right), \quad \text{Equation 6}$$

$$(0 \leq b \leq 1)$$

In Equation 6, $\text{score}_{res}$ is a second numerical value, $res_n$ is a normalized residual value, and $res_{max}$ and $res_{min}$ denote values set in advance for obtaining the second numerical value. Further, "b" may represent a maximum value according to a weight for the second numerical value from among reliability values. For example, the second numerical value may be equal to or greater than 0 and equal to or less than two (2). In particular, in the case in which the reliability value is represented by a numerical value equal to or greater than 0 and equal to or less than 1, sum of "a" and "b" may be 1. For example, "a" may be equal to 0.2, and "b" may be equal to 0.8.

Then, in operation S5500, the ultrasound imaging apparatus 350 may sum the first numerical value and the second numerical value. In operation S5600, the ultrasound imaging apparatus 350 may determine a result of summing the first numerical value and the second numerical value in operation S5500 as a reliability value.

Figure 6:
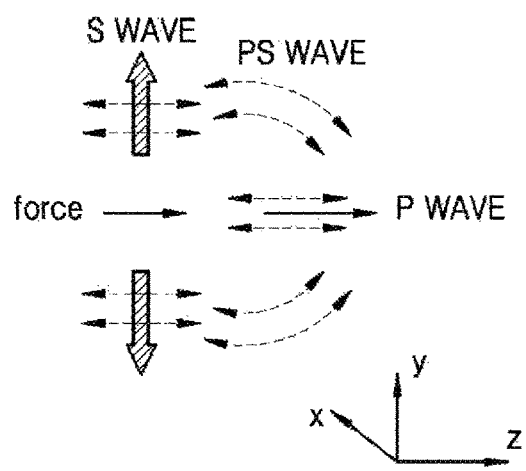
FIG. 6 is a diagram for explaining a shear wave.

FIG. 6 is a diagram for explaining a shear wave.

Referring to FIG. 6, in the case in which a force of a point impulse is exerted in a z-axis direction, a "p" wave, which is a longitudinal wave, an "s" wave, which is a transverse wave, and a "ps" wave, in which the two waves are coupled, are generated. In particular, the shear wave is an "s" wave that vibrates in a wave progression direction and progresses in a y-axis direction from a vibration source by which the force is exerted.

Figure 7:
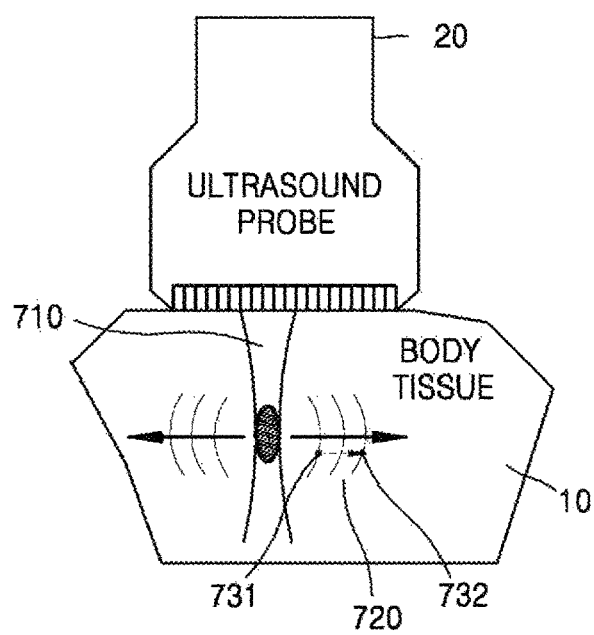
FIG. 7 is a diagram for explaining a shear wave generated inside an object.

FIG. 7 is a diagram for explaining a shear wave generated inside an object.

As illustrated in FIG. 7, the ultrasound imaging apparatus 350 may transmit, to an object 10, an ultrasound signal 710 (referred to as a "push ultrasound signal", for convenience of description) for pushing a portion of the object 10. For example, the ultrasound imaging apparatus 350 may transmit the push ultrasound signal 710, which has a relatively long wavelength, to the object 10 by using some of channels of the probe 20. According to an exemplary embodiment, the ultrasound imaging apparatus 350 may transmit the focused push ultrasound signal 710 to a portion of the object 10.

In this case, a shear wave 720 may be generated by the push ultrasound signal 710 inside the object 10. For example, the shear wave 720 may be generated with a relatively close proximity to a region pushed by the push ultrasound signal 710. The shear wave 720 may propagate at a velocity of between about 1 m/s and about 10 m/s. Since the velocity of the shear wave 720 is very slow compared with an average velocity (e.g., about 1540 m/s) of an ultrasound signal inside the object 10, the ultrasound imaging apparatus 350 may use an ultrasound signal (hereinafter referred to as a "tracking ultrasound signal") in order to track the shear wave 720. For example, the ultrasound imaging apparatus 350 may track the velocity of the shear wave 720 by transmitting a tracking ultrasound signal in a progression direction of the shear wave 720. In this case, the wavelength of a tracking ultrasound signal may be shorter than the wavelength of the push ultrasound signal 710.

Figure 8:
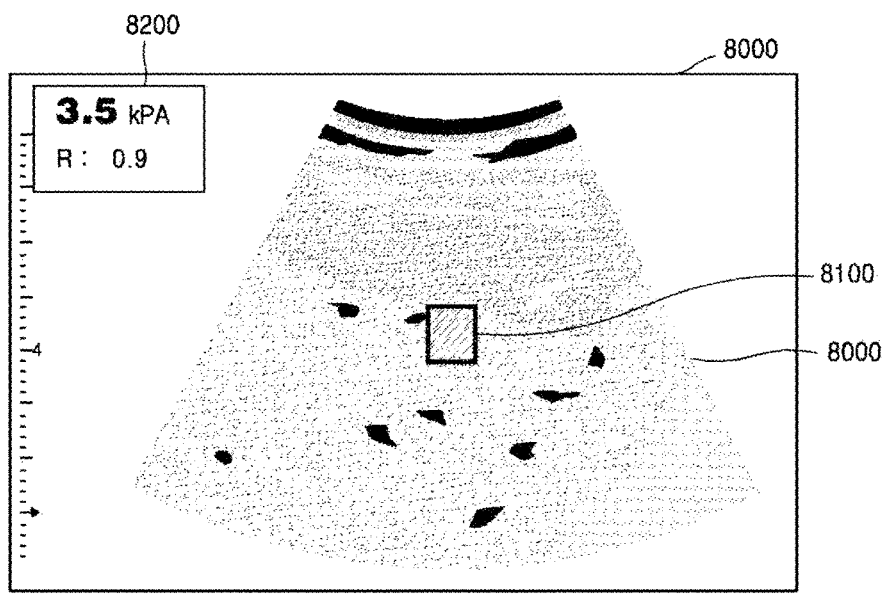
FIG. 8 is a diagram illustrating a screen displayed by an ultrasound imaging apparatus, according to an exemplary embodiment.

FIG. 8 is a diagram illustrating a screen displayed by an ultrasound imaging apparatus 350, according to an exemplary embodiment.

The ultrasound imaging apparatus 350 according to an exemplary embodiment may display an ultrasound image 8000. In particular, when a region of interest (ROI) 8100 is set inside the ultrasound image 8000 based on a user input, the ultrasound imaging apparatus 350 may calculate an elasticity value for the set region of interest, and may determine a reliability value that relates to the elasticity value. The ultrasound imaging apparatus 350 may display a reliability value as a numerical value. The ultrasound imaging apparatus 350 may display the calculated elasticity value and reliability value 8200 as illustrated in FIG. 8. FIG. 8 is a diagram illustrating the case in which an elasticity value is about 3.5 kPa and a reliability value is about 0.9.

Figure 9:
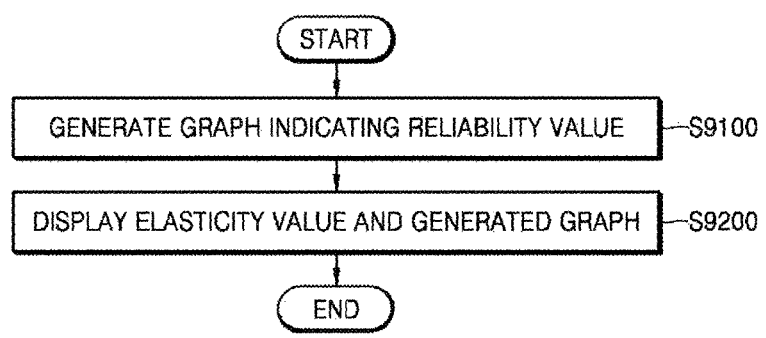
FIG. 9 is a flowchart illustrating a process of displaying a reliability value in an ultrasound imaging apparatus, according to an exemplary embodiment.
Figure 10:
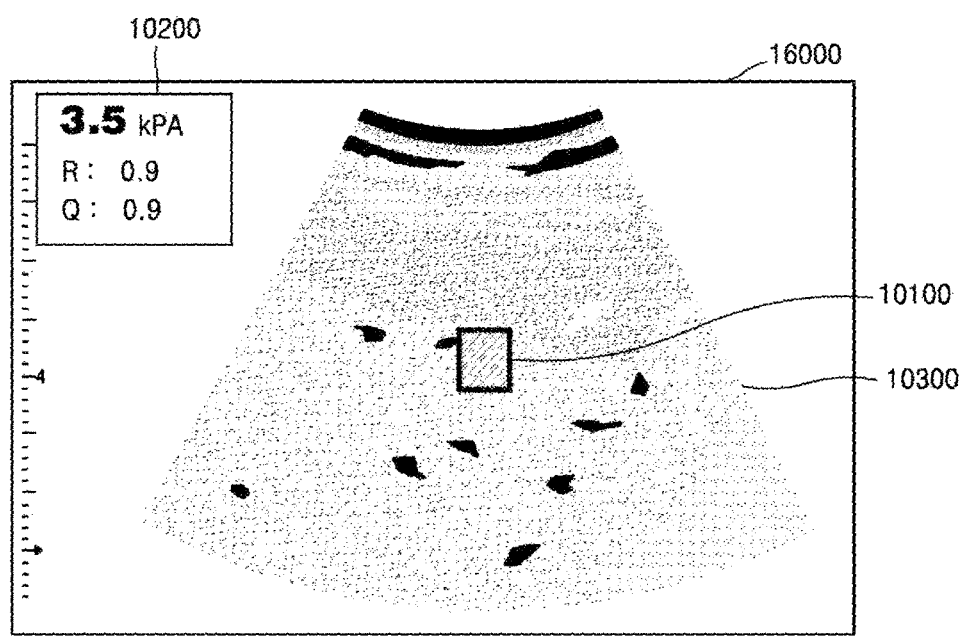
FIG. 10 is a diagram illustrating another screen displayed by an ultrasound imaging apparatus, according to an exemplary embodiment.
Figure 11:
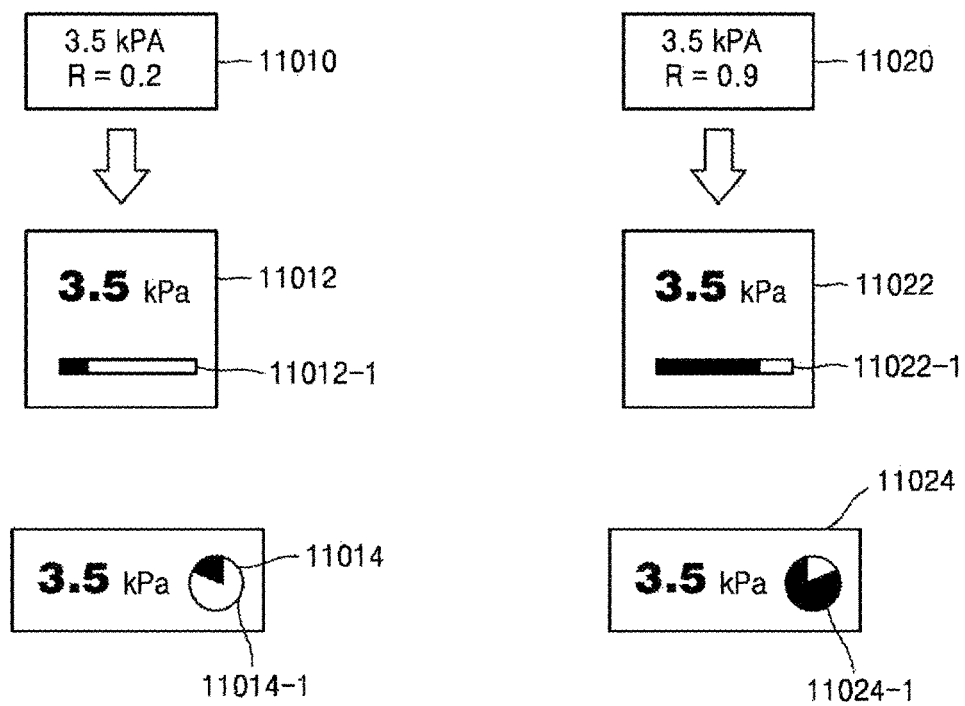
FIG. 11 is a diagram for explaining a graph displayed by an ultrasound imaging apparatus, according to an exemplary embodiment.

FIG. 9 is a flowchart illustrating a process of displaying a reliability value in an ultrasound imaging apparatus according to an exemplary embodiment, FIG. 10 is a diagram illustrating a screen displayed by an ultrasound imaging apparatus according to an exemplary embodiment, and FIG. 11 is a diagram for explaining a graph displayed by an ultrasound imaging apparatus according to an exemplary embodiment.

According to an exemplary embodiment, in operation S9100, the ultrasound imaging apparatus 350 may generate a graph that indicates a reliability value which is determined based on an obtained elasticity value. Then, in operation S9200, the ultrasound imaging apparatus 350 may display the obtained elasticity value and the generated graph.

Referring to FIG. 10, when a region 10100 of interest is set with respect to an ultrasound image 10300, the ultrasound imaging apparatus may display a block 10200 which includes characters that respectively represent an elasticity value and a reliability value. Though FIG. 10 displays a reliability value as letters, the reliability value may be represented by any of various shapes based on an exemplary embodiment. In particular, the ultrasound imaging apparatus 350 may generate a graph that includes at least one from among a dot, a straight line, a curve, a bar, a circle, and a figure, and that represents a reliability value. Referring to FIG. 11, in the case 11010 where an elasticity value is approximately equal to 3.5 kPa and a reliability value is approximately equal to 0.2, the ultrasound imaging apparatus 350 may display an elasticity value and a reliability value 11012 by using a bar 11012-1 having a length which corresponds to about 0.2, or may display an elasticity value and a reliability value 11014 by using a portion 11014-1 of a circle having an area that corresponds to about 0.2. Further, in the case 11020 in which an elasticity value is approximately equal to 3.5 kPa and a reliability value is approximately equal to 0.9, the ultrasound imaging apparatus 350 may display an elasticity value and a reliability value 11022 by using a bar 11022-1 having a length that corresponds to about 0.9, or may display an elasticity value and a reliability value 11024 by using a portion 11024-1 of a circle having an area that corresponds to about 0.9.

Figure 12:
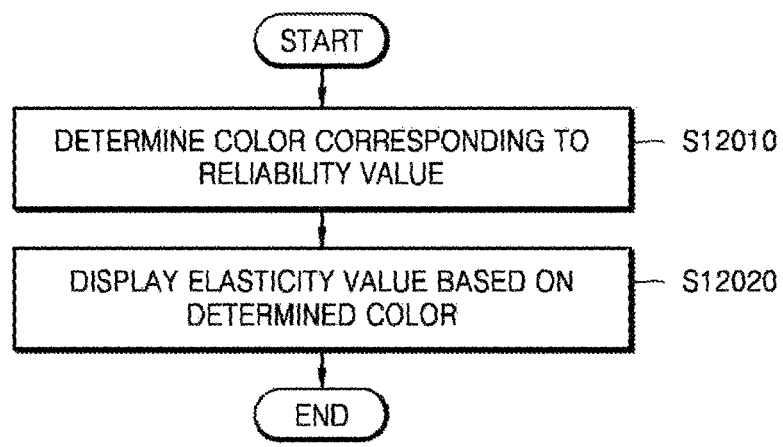
FIG. 12 is a flowchart illustrating a process for displaying a reliability value in an ultrasound imaging apparatus, according to an exemplary embodiment.

FIG. 12 is a flowchart illustrating a process for displaying a reliability value in an ultrasound imaging apparatus 350, according to an exemplary embodiment.

According to an exemplary embodiment, in operation S12010, the ultrasound imaging apparatus 350 may determine a color that corresponds to a reliability value based on a magnitude of the determined reliability value. For example, the ultrasound imaging apparatus 350 may determine that a red color is a color that corresponds to a reliability value when a magnitude of the reliability value is less than 0.3, determine that a yellow color is a color that corresponds to a reliability value when a magnitude of the reliability value is equal to or greater than 0.3 and less than 0.6, and determine that a green color is a color that corresponds to a reliability value when a magnitude of the reliability value is equal to or greater than 0.6.

Then, in operation S12020, the ultrasound imaging apparatus 350 may display an elasticity value based on the color determined in operation S12010. For example, in the case in which an elasticity value is displayed in the red color, a user may recognize that the reliability of the elasticity value is relatively low.

Figure 13:
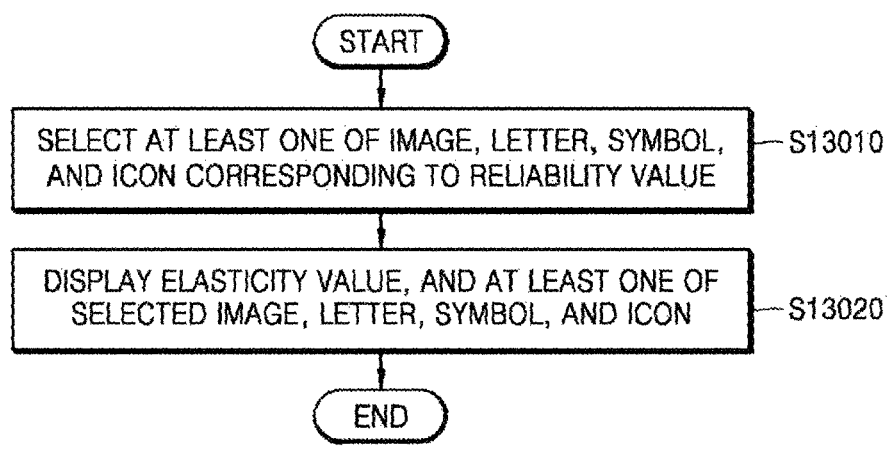
FIG. 13 is a flowchart illustrating a process for displaying a reliability value in an ultrasound imaging apparatus, according to an exemplary embodiment.
Figure 14:
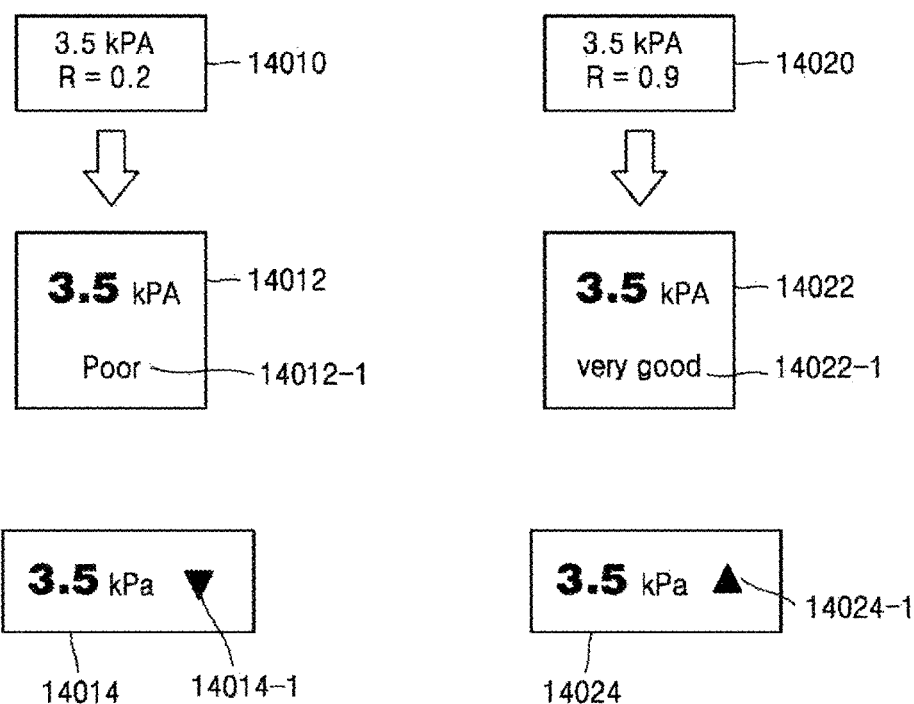
FIG. 14 is a diagram for explaining a method for displaying a reliability value in an ultrasound imaging apparatus, according to an exemplary embodiment.

FIG. 13 is a flowchart illustrating a process for displaying a reliability value in an ultrasound imaging apparatus 350 according to an exemplary embodiment, and FIG. 14 is a diagram for explaining a method for displaying a reliability value in an ultrasound imaging apparatus 350 according to an exemplary embodiment.

According to an exemplary embodiment, in operation S13010, the ultrasound imaging apparatus 350 may select at least one from among an image, one or more letters or words, a symbol, and an icon that corresponds to a reliability value. In this aspect, the image, the letter, the symbol, and the icon are only exemplary, and may be replaced by an arbitrary object that may be visually displayed.

Then, in operation S13020, the ultrasound imaging apparatus 350 may display the selected at least one from among an elasticity value, the selected image, letter(s) or word(s), symbol, and icon.

Referring to FIG. 14, when an elasticity value is 3.5 kPa and a reliability value is 0.2 (14010), the ultrasound imaging apparatus 350 may display the elasticity value and the reliability value 14012 by using a word "poor" (14012-1), which represents that the reliability of an elasticity value is relatively bad. Alternatively, the ultrasound imaging apparatus 350 may display the elasticity value and the reliability value 14014 by using a symbol 14014-1 that represents that the reliability of an elasticity value is relatively low. Further, when an elasticity value is 3.5 kPa and a reliability value is 0.9 (14020), the ultrasound imaging apparatus 350 may display the elasticity value and the reliability value 14022 by using the words "very good" (14022-1), which represents that the reliability of an elasticity value is relatively good. Alternatively, the ultrasound imaging apparatus 350 may display the elasticity value and the reliability value 14024 by using a symbol 14024-1 that represents that the reliability of an elasticity value is relatively high.

Further, the ultrasound imaging apparatuses 300 and 350 according to an exemplary embodiment may determine the quality of a shear wave observed in response to the induced shear wave. For example, the controller 310 may determine the quality of the shear wave.

In this aspect, the quality of the shear wave denotes the quality of the shear wave itself induced to the object 10. The quality of the shear wave may be determined based on a degree of a noise component that exists in the observed shear wave. In particular, when a noise component is relatively small with respect to a shear wave, the controller 310 may determine that the quality of the shear wave is relatively high, and when a noise component is relatively large with respect to a shear wave, the controller 310 may determine that the quality of the shear wave is relatively high.

More particularly, the quality of the shear wave may be calculated based on a signal-to-noise ratio (SNR) of the observed shear wave.

Referring to FIG. 7, one point 731 inside the object 10 is moved by a shear wave 720 induced to the object 10. In particular, a maximum distance up to a point 732 to which the one point 731 inside the object 10 is moved is referred to as displacement. The quality of the shear wave may be calculated based on a measured displacement.

For example, the quality of the shear wave may be determined based on a calculated displacement profile. According to an exemplary embodiment, a signal-to-noise ratio (SNR) of displacement which varies as a function of time may be determined as the quality of the shear wave. According to an exemplary embodiment, when a displacement occurring while a predetermined point inside the object 10 moves is expressed as an amplitude after the shear wave is induced inside the object 10, an amplitude graph with respect to time may be referred to as a displacement profile. The quality of the shear wave may extract a high frequency component as a noise component in a displacement profile. Further, an SNR of a displacement may be determined by calculating a root mean square (RMS) value of the extracted noise component as a signal value of a noise component, and calculating the remaining components that exclude the high frequency component as a signal component in a displacement profile.

Further, the quality of a shear wave may be calculated by using any of various methods that may quantify a noise component inside the shear wave.

In addition, the quality of a shear wave may be determined on a point or region basis, such as a quality determination with respect to at least one point inside an object or a predetermined region of the object, for example, a region of interest (ROI), and/or any other suitable portion of the object.

The following description is based on the case of obtaining the quality of a shear wave in a region of interest (ROI) as an example.

The display 320 may display a user interface screen which includes a representation of the quality of a shear wave. According to an exemplary embodiment, the display 320 may display a user interface screen which includes a respective representation of each of an obtained elasticity value, a reliability value that relates to the obtained elasticity value, and the determined quality of a shear wave under control of the controller 310. In particular, the user interface screen may include information which represents each of an ultrasound image, an obtained elasticity value, a reliability value of the obtained elasticity value, and the quality of a shear wave on one screen.

Examples of a user interface screen output based on an exemplary embodiment are described below with reference to FIGS. 15 to 20.

Figure 15:
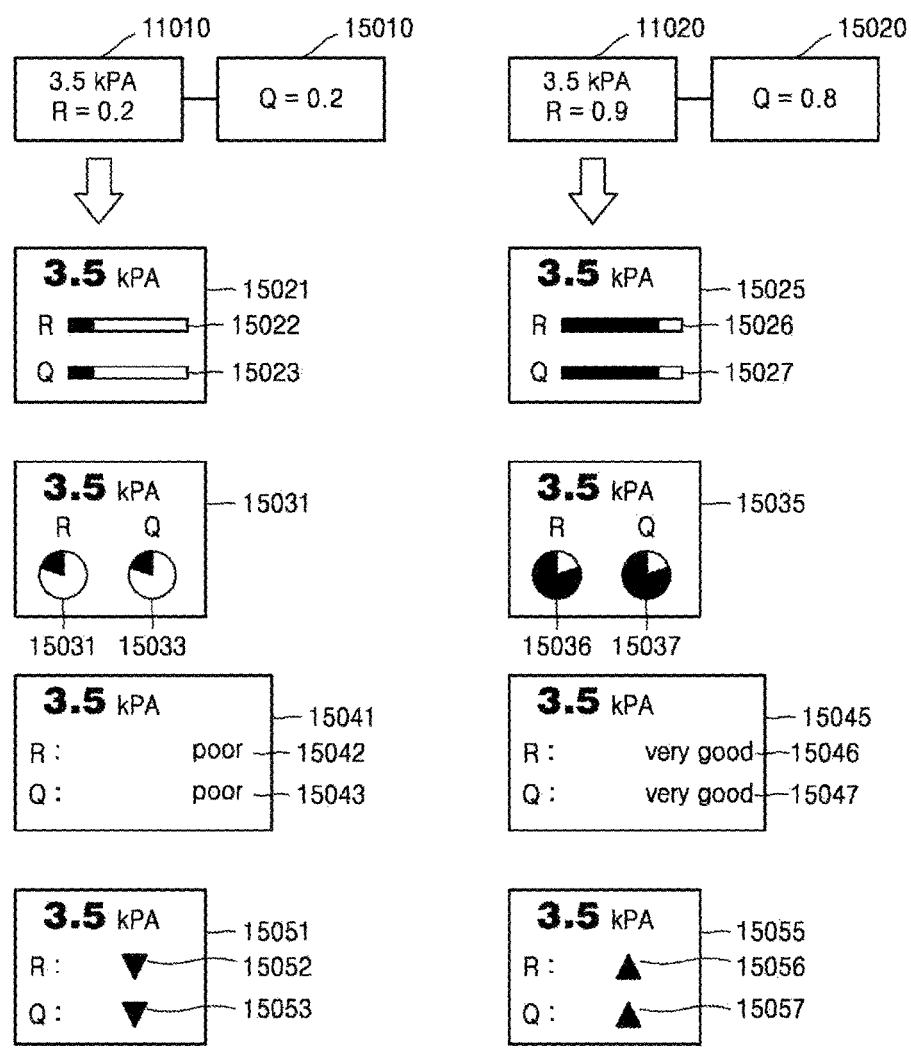
FIG. 15 is a diagram for explaining a method for displaying a reliability value and quality in an ultrasound imaging apparatus, according to an exemplary embodiment.

FIG. 15 is a diagram for explaining a method for displaying a reliability value and quality in an ultrasound imaging apparatus 350, according to an exemplary embodiment.

Referring to FIG. 15, the ultrasound imaging apparatus 350 may generate and display information that represents the quality of a shear wave in addition to an operation of the ultrasound imaging apparatus 350 illustrated in FIG. 11. According to an exemplary embodiment, the ultrasound imaging apparatus 350 may generate and display information that represents the quality of a shear wave in addition to the generating and displaying of the reliability value as illustrated in FIG. 11. In FIG. 15, like reference numerals are used for the like components of FIG. 11.

In FIG. 15, a quality value 15010 of a shear wave obtained by the ultrasound imaging apparatus 350 is represented by "Q", and a reliability value is represented by "R". Further, the case in which a quality value 15010 of a shear wave is converted and displayed so that the quality value 15010 of the shear wave may have a value between 0 and 1 is exemplarily illustrated.

Referring to FIG. 15, the ultrasound imaging apparatus 350 may generate a graph which includes at least one from among a dot, a straight line, a curve, a bar, a circle, and a figure, and which represents each of a reliability value and a quality value. Referring to FIG. 15, the case in which an elasticity value is about 3.5 kPa, a reliability value is about 0.2 (11010), and a quality value 15010 is about 0.2 is exemplarily illustrated.

Referring to a block 15021, the ultrasound imaging apparatus 350 may display a reliability value R by using a bar 15022 having a length that corresponds to about 0.2, and display a quality value Q by using a bar 15023 having a length that corresponds to about 0.2.

Further, referring to a block 15031, the ultrasound imaging apparatus 350 may display a reliability value R by using a portion 15032 of a circle having an area that corresponds to about 0.2, and display a quality value Q by using a portion 15033 of a circle having an area that corresponds to about 0.2.

In addition, the ultrasound imaging apparatus 350 may display a reliability value and a quality value by using a symbol or one or more letters or words which represent that the reliability of an elasticity value is good or bad, and a symbol or one or more letters or words which represent that a quality value of a shear wave is good or bad.

According to an exemplary embodiment, referring to a block 15041, when an elasticity value is about 3.5 kPa, a reliability value is about 0.2, and a quality value is about 0.2, the ultrasound imaging apparatus 350 may display a reliability value R by using a word "poor" 15042 which represents that the reliability of an elasticity value is relatively bad, and display a quality value Q by using a word "poor" 15043 which represents that the quality of a shear wave is relatively bad.

Further, referring to a block 15051, when an elasticity value is about 3.5 kPa, a reliability value is about 0.2, and a quality value is about 0.2, the ultrasound imaging apparatus 350 may display a reliability value R by using a symbol V 15052 which represents that the reliability of an elasticity value is relatively bad, and display a quality value Q by using a symbol V 15053 which represents that the quality of a shear wave is relatively bad.

In addition, referring to FIG. 15, the case in which an elasticity value is about 3.5 kPa, a reliability value is about 0.9 (11020), and a quality value (15020) is about 0.8 is exemplarily illustrated.

Referring to a block 15025, the ultrasound imaging apparatus 350 may display a reliability value R by using a bar 15026 having a length that corresponds to about 0.9, and display a quality value Q by using a bar 15027 having a length that corresponds to about 0.8.

Further, referring to a block 15035, the ultrasound imaging apparatus 350 may display a reliability value R by using a portion 15036 of a circle having an area that corresponds to about 0.9, and display a quality value Q by using a portion 15037 of a circle having an area that corresponds to about 0.8.

Still further, the ultrasound imaging apparatus 350 may display a reliability value and a quality value by using a symbol or one or more letters or words which represent that the reliability of an elasticity value is good or bad, and a symbol or one or more letters or words which represent that a quality value of a shear wave is good or bad.

According to an exemplary embodiment, referring to a block 15045, when an elasticity value is about 3.5 kPa, a reliability value is about 0.9, and a quality value is about 0.8, the ultrasound imaging apparatus 350 may display a reliability value R by using the words "very good" 15046, which represent that the reliability of an elasticity value is relatively high, and display a quality value Q by using the words "very good" 15047, which represent that the quality of a shear wave is relatively good.

Further, referring to a block 15055, when an elasticity value is about 3.5 kPa, a reliability value is about 0.9, and a quality value is about 0.8, the ultrasound imaging apparatus 350 may display a reliability value R by using a symbol Δ 15056 which represents that the reliability of an elasticity value is relatively high, and display a quality value Q by using a symbol Δ 15057 which represents that the quality of a shear wave is relatively good.

Still further, the ultrasound imaging apparatus 350 may display each of a reliability value and an elasticity value by combining at least one of the above-described graph, numerical value, letter, and symbol.

In addition, the ultrasound imaging apparatus 350 may display a reliability value and an elasticity value on one screen together with an ultrasound image. An ultrasound image included in the screen may be the above-described A mode image, B mode image, M mode image, elasticity image, Doppler image, etc. Further, an ultrasound image included in the screen may be an image that combines the B mode image, the elasticity image, or the Doppler image with the elasticity image. For example, an ultrasound image displayed on the screen of the ultrasound imaging apparatus 350 may be an image in which the elasticity image overlaps an ROI of the B mode image.

Exemplary embodiments of a screen displayed by the ultrasound imaging apparatus 350 are described below with reference to FIGS. 16 to 20. FIGS. 16 to 20 exemplarily illustrate the case where an elasticity value is about 3.5 kPa, a reliability value R is about 0.9, and a quality value Q is about 0.9.

Figure 16:
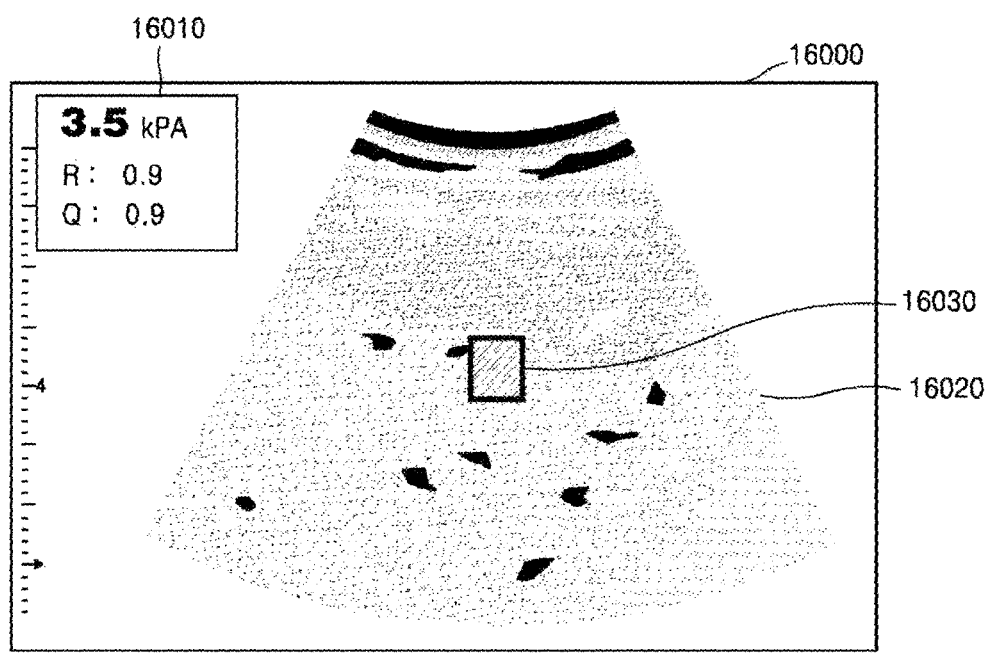
FIG. 16 is a diagram illustrating another screen displayed by an ultrasound imaging apparatus, according to an exemplary embodiment.

FIG. 16 is a diagram illustrating another screen 16000 displayed by an ultrasound imaging apparatus 350, according to an exemplary embodiment.

Referring to FIG. 16, the screen 16000 displayed by the ultrasound imaging apparatus 350 includes an ultrasound image 16020, and a box 16010 that displays an elasticity value, a reliability value, and a quality value. In particular, the elasticity value, the reliability value, and the quality value displayed in the box 16010 may be displayed numerically. Further, the elasticity value, the reliability value, and the quality value displayed in the box 16010 may be values that correspond to a region 16030 of interest inside the ultrasound image 16020. In addition, the elasticity value, the reliability value, and the quality value displayed in the box 16010 may be an elasticity value, a reliability value, and a quality value that correspond to one specific point inside the ultrasound image 16020, respectively.

Figure 17:
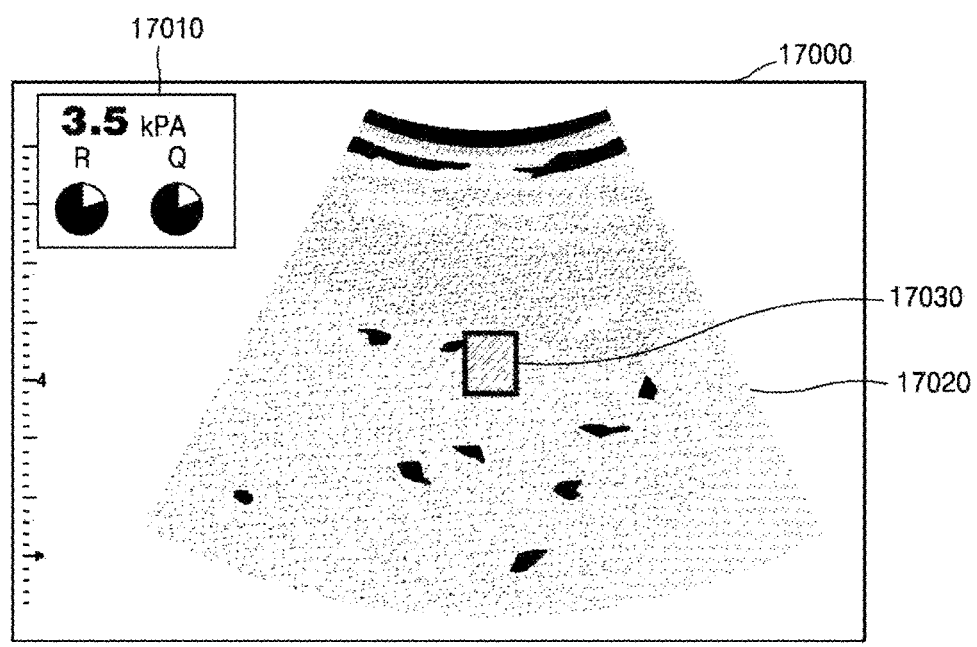
FIG. 17 is a diagram illustrating another screen displayed by an ultrasound imaging apparatus, according to an exemplary embodiment.

FIG. 17 is a diagram illustrating another screen 17000 displayed by an ultrasound imaging apparatus 350, according to an exemplary embodiment.

Referring to FIG. 17, the screen 17000 displayed by the ultrasound imaging apparatus 350 includes an ultrasound image 17020, and a box 17010 that displays an elasticity value, a reliability value, and a quality value. In particular, the elasticity value may be displayed numerically, and the reliability value and the quality value displayed in the box 17010 may be displayed in the form of a graph. According to an exemplary embodiment, as described in FIG. 15, the reliability value and the quality value may be displayed by using a graph which includes at least one from among a dot, a straight line, a curve, a bar, a circle, and a figure. Further, the elasticity value, the reliability value, and the quality value displayed in the box 17010 may be values that correspond to a region 17030 of interest inside the ultrasound image 17020.

Figure 18:
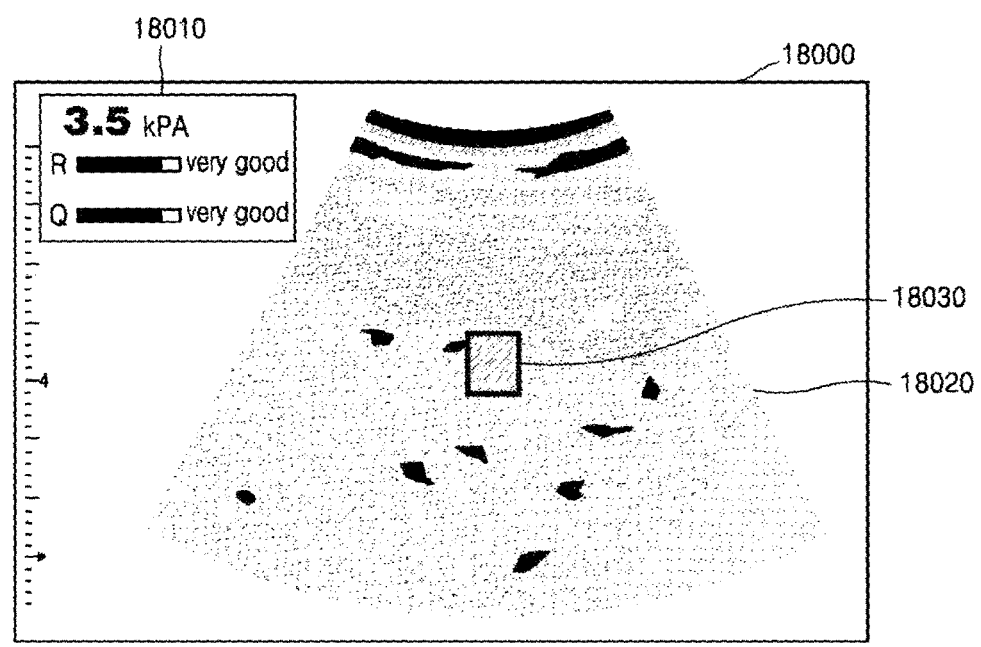
FIG. 18 is a diagram illustrating another screen displayed by an ultrasound imaging apparatus, according to an exemplary embodiment.

FIG. 18 is a diagram illustrating another screen 18000 displayed by an ultrasound imaging apparatus 350, according to an exemplary embodiment.

Referring to FIG. 18, the screen 18000 displayed by the ultrasound imaging apparatus 350 includes an ultrasound image 18020, and a box 18010 that displays an elasticity value, a reliability value, and a quality value. In particular, the elasticity value may be displayed numerically, and the reliability value and the quality value displayed in the box 18010 may be displayed in the form that combines a graph with words.

For example, referring to the box 18010, a reliability value and a quality value may be displayed by combining the bar graph illustrated in the block 15025 of FIG. 15 with the words illustrated in the block 15045 of FIG. 15. Further, the elasticity value, the reliability value, and the quality value displayed in the box 18010 may be values that correspond to a region 18030 of interest inside the ultrasound image 18020.

Figure 19:
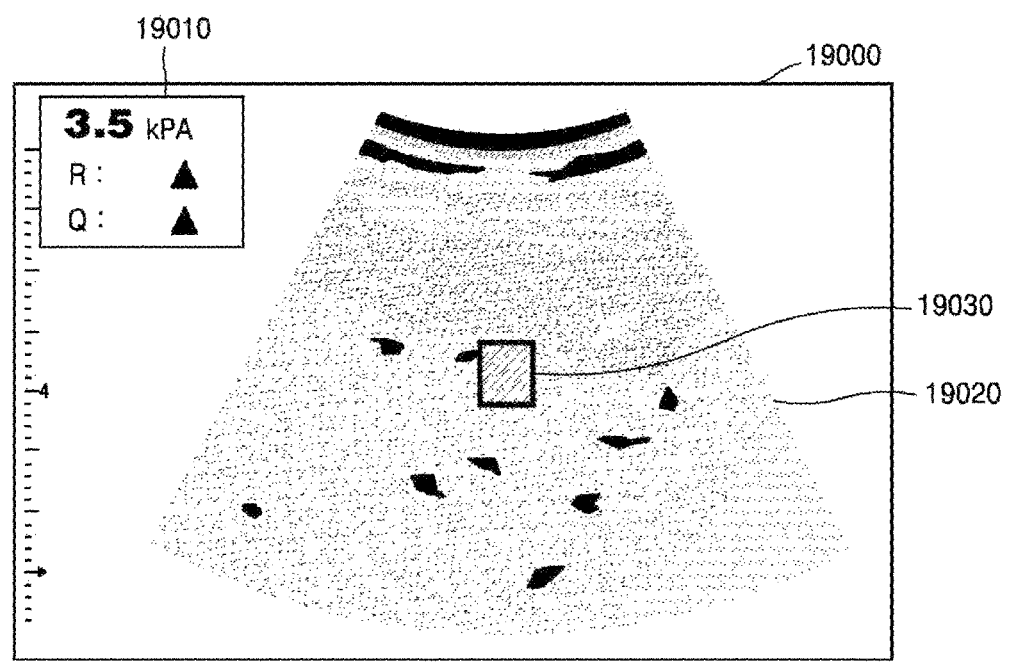
FIG. 19 is a diagram illustrating another screen displayed by an ultrasound imaging apparatus, according to an exemplary embodiment.

FIG. 19 is a diagram illustrating another screen 19000 displayed by an ultrasound imaging apparatus 350, according to an exemplary embodiment.

Referring to FIG. 19, the screen 19000 displayed by the ultrasound imaging apparatus 350 includes an ultrasound image 19020, and a box 19010 that displays an elasticity value, a reliability value, and a quality value. In particular, the reliability value and the quality value displayed in the region 19010 may be displayed by using a symbol which represents that the reliability value and the quality value are either good or bad.

For example, referring to the box 19010, the reliability value and the quality value may be displayed by using the symbol illustrated in the block 15055 of FIG. 15. Further, the elasticity value, the reliability value, and the quality value displayed in the box 19010 may be values that correspond to a region 19030 of interest inside the ultrasound image 19020.

Figure 20:
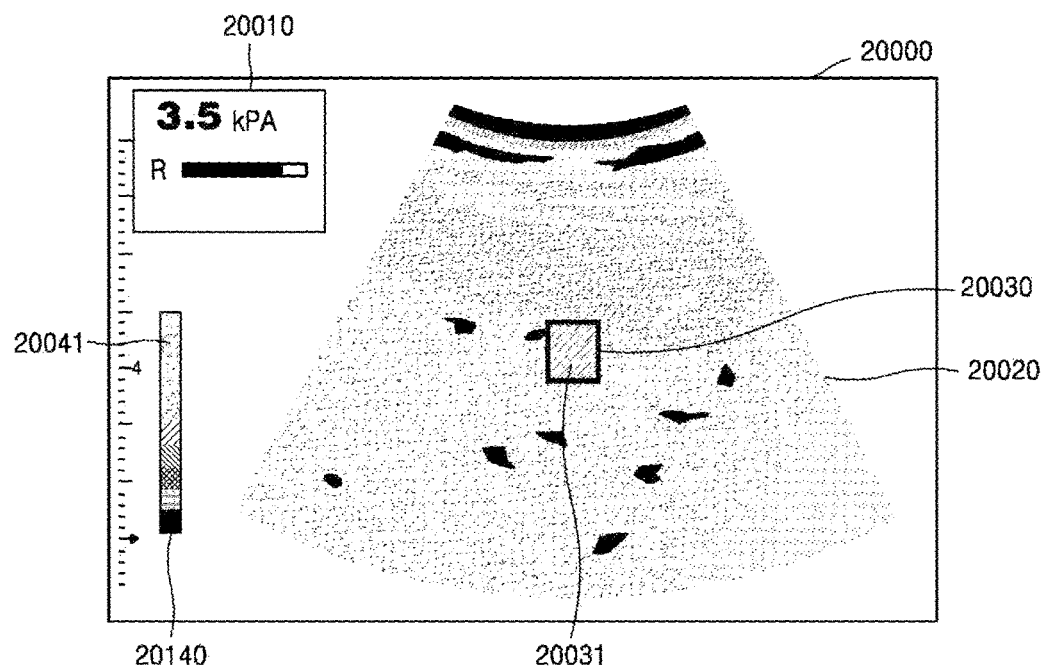
FIG. 20 is a diagram illustrating another screen displayed by an ultrasound imaging apparatus, according to an exemplary embodiment.

FIG. 20 is a diagram illustrating another screen 20000 displayed by an ultrasound imaging apparatus 350, according to an exemplary embodiment.

Referring to FIG. 20, the screen 20000 displayed by the ultrasound imaging apparatus 350 includes an ultrasound image 20020, and a box 20010 that displays an elasticity value and a reliability value. Further, a quality value may be displayed on a region 20030 of interest in a color level or a gray level 20031 that corresponds to the quality value. According to an exemplary embodiment, the screen 20000 may display a color scale or a gray scale 20040 which represents a quality value. For example, FIG. 20 illustrates the case where the color scale 20040 which represents a quality value expressed in a value between 0 and 1 is displayed, and a quality value is displayed on the region 20030 of interest by using a color 20041 that corresponds to a value of 0.9 on the color scale 20040.

As described above, the ultrasound imaging apparatus according to an exemplary embodiment may calculate a reliability of an obtained elasticity value more accurately by determining the reliability of the elasticity value by using a residual value.

Further, the ultrasound imaging apparatus according to an exemplary embodiment may output a user interface screen that enables a user to recognize a reliability value, or a reliability value and a quality value more intuitively.

Exemplary embodiments may be implemented in the form of a recording medium which includes a command that is executable by a computer, such as a program module executed by a computer. A non-transitory computer-readable medium may be an arbitrary available medium that may be accessed by a computer, and include all of a volatile medium, a non-volatile medium, a separation type medium, and a non-separation type medium. Further, a non-transitory computer-readable medium may include both a computer storage medium and a communication medium. The computer storage medium includes all of a volatile medium, a non-volatile medium, a separation type medium, and a non-separation type medium implemented by using an arbitrary method or technology for storing information, such as a computer-readable command, a data structure, a program module, or other data. The communication medium may include a computer-readable command, a data structure, a program module, or other data of a modulated data signal, or other transmission mechanisms, and include an arbitrary information transfer medium.

The above explanation is provided for exemplary purposes, and a person of ordinary skill in the art will understand that other specific changes may be easily made without changing the technical spirit or the essential characteristic of the present inventive concept. Therefore, the above described exemplary embodiments should be understood as being exemplary in all aspects, not being limited. For example, each component described as a single form may be distributed and implemented, and likewise, components described as being distributed may be implemented in the form of a combination.

The scope of the present inventive concept is defined by the following claims rather than the above detailed descriptions, and it should be construed that all modifications or changed forms derived from the meaning and scope of the claims and the equivalent concept thereof are included in the scope of the present inventive concept.

What is claimed is:

1. A method for processing an ultrasound image, the method comprising:
    inducing a shear wave inside an object;
    obtaining an ultrasound image of the object after inducing the shear wave;
    obtaining an elasticity value of the object based on the obtained ultrasound image;
    obtaining a residual value of a wave equation based on the obtained elasticity value and at least one of a particle velocity and a particle displacement;
    determining a reliability value based on a magnitude of the induced shear wave and the obtained residual value; and
    displaying, on a display, a respective representation of each of the obtained elasticity value and the determined reliability value.

2. The method of claim 1, wherein the displaying comprises:
    displaying at least one from among an image, a letter, an icon, and a symbol that corresponds to a magnitude of the determined reliability value.

3. The method of claim 1, wherein the displaying comprises:
    displaying a screen which comprises an elasticity image generated based on the induced shear wave, the obtained elasticity value, and the determined reliability value.

4. The method of claim 1, further comprising:
    setting a region of interest (ROI) with respect to the object,
    wherein the obtaining the elasticity value comprises:
    obtaining an elasticity value that relates to the object inside the region of interest based on an observation of the induced shear wave with respect to an inside of the ROI.

5. A non-transitory computer-readable recording medium having recorded thereon a program that is executable for performing the method of claim 1.

6. An ultrasound imaging apparatus comprising:
    a controller configured to obtain an elasticity value of an object based on an ultrasound image which is obtained after inducing a shear wave inside the object, to obtain a residual value of a wave equation based on the obtained elasticity value and at least one of a particle velocity and a particle displacement, and to determine a reliability value based on a magnitude of the induced shear wave and the obtained residual value; and
    a display configured to display a respective representation of each of the obtained elasticity value and the determined reliability value.

7. The apparatus of claim 6, wherein the controller is further configured to determine the reliability value based on a result of a comparison between the obtained elasticity value and the reference value.

8. The apparatus of claim 6, wherein the controller is further configured to obtain the residual value that corresponds to a difference between the obtained elasticity value and a reference value, and to determine the reliability value based on a magnitude of the induced shear wave and the obtained residual value,
    wherein the reference value is determined by applying at least one from among the particle displacement value and the particle velocity value of the induced shear to a predetermined equation.

9. The apparatus of claim 6, wherein the controller is further configured to obtain the residual value that corresponds to an error of the shear wave with respect to the predetermined wave equation when the at least one from among the particle displacement value and the particle velocity value of the shear wave is applied to the predetermined wave equation, and to determine the reliability value based on a magnitude of the induced shear wave and the obtained residual value.

10. The apparatus of claim 6, wherein the controller is further configured to determine a magnitude of the induced shear wave that corresponds to the elasticity value, to calculate a first numerical value based on the determined magnitude of the shear wave, to calculate a second numerical value based on a result of a comparison between the obtained elasticity value and the reference value, and to determine the reliability value based on the calculated first numerical value and the calculated second numerical value.

11. The apparatus of claim 10, wherein the controller is further configured to calculate the second numerical value based on the residual value that corresponds to a difference between the obtained elasticity value and the reference value.

12. The apparatus of claim 10, wherein the reliability value is equal to or greater than zero and equal to or less than one.

13. The apparatus of claim 6, further comprising:
an ultrasound transceiver configured to induce the shear wave inside the object, and to observe the induced shear wave.

14. The apparatus of claim 6, further comprising:
a communication module configured to receive the induced shear wave from a wireless probe.

15. The apparatus of claim 6, wherein the display is further configured to display the representation of the determined reliability value by using a numerical value.

16. The apparatus of claim 6, wherein the display is further configured to display a graph which indicates a magnitude of the determined reliability value.

17. The apparatus of claim 6, wherein the display is further configured to display the representation of the obtained elasticity value by using a color that corresponds to a magnitude of the determined reliability value.

18. The apparatus of claim 6, wherein the display is further configured to display at least one from among an image, a letter, an icon, and a symbol that corresponds to a magnitude of the determined reliability value.

19. The apparatus of claim 6, wherein the controller is further configured to determine a quality of the induced shear wave based on a displacement characteristic of the shear wave.

20. The apparatus of claim 19, wherein the display is further configured to display a user interface screen which includes a respective representation of each of the obtained elasticity value, the determined reliability value, and the determined quality.

* * * * *